US009012474B2

(12) United States Patent
Murthy

(10) Patent No.: US 9,012,474 B2
(45) Date of Patent: Apr. 21, 2015

(54) FLUOROQUINOLONE COMPOSITIONS

(75) Inventor: Yerramilli V. S. N. Murthy, Apex, NC (US)

(73) Assignee: Idexx Laboratories Inc., Westbrook, ME (US)

( * ) Notice: Subject to any disclaimer, the term of this patent is extended or adjusted under 35 U.S.C. 154(b) by 1558 days.

(21) Appl. No.: 12/210,566

(22) Filed: Sep. 15, 2008

(65) Prior Publication Data

US 2009/0012072 A1   Jan. 8, 2009

Related U.S. Application Data

(63) Continuation of application No. 11/356,206, filed on Feb. 17, 2006, now abandoned.

(51) Int. Cl.
| | | |
|---|---|---|
| A61K 31/4709 | (2006.01) | |
| A61K 31/496 | (2006.01) | |
| A61K 47/40 | (2006.01) | |
| A61K 47/02 | (2006.01) | |
| A61K 47/12 | (2006.01) | |
| A61K 9/00 | (2006.01) | |
| A61K 9/08 | (2006.01) | |
| A61K 47/10 | (2006.01) | |

(52) U.S. Cl.
CPC .......... *A61K 31/4709* (2013.01); *A61K 9/0019* (2013.01); *A61K 9/0095* (2013.01); *A61K 9/08* (2013.01); *A61K 31/496* (2013.01); *A61K 47/02* (2013.01); *A61K 47/10* (2013.01); *A61K 47/12* (2013.01); *A61K 47/40* (2013.01)

(58) Field of Classification Search
CPC . A61K 31/4709; A61K 31/496; A61K 47/40; A61K 47/02; A61K 47/12
USPC .................................................. 514/311, 759
See application file for complete search history.

(56) References Cited

U.S. PATENT DOCUMENTS

| | | |
|---|---|---|
| 4,292,317 A | 9/1981 | Pesson |
| 4,448,962 A | 5/1984 | Irikura et al. |
| 4,499,091 A | 2/1985 | Wentland et al. |
| 4,668,784 A | 5/1987 | Mascellani et al. |
| 4,704,459 A | 11/1987 | Todo et al. |
| 4,795,751 A | 1/1989 | Matsumoto et al. |
| 4,957,922 A | 9/1990 | Lammens et al. |
| 5,077,429 A | 12/1991 | Grobe et al. |
| 5,334,589 A | 8/1994 | Al-Razzak et al. |
| 5,464,796 A | 11/1995 | Peterson et al. |
| 5,476,854 A | 12/1995 | Young |
| 5,532,239 A | 7/1996 | Pruna |
| 5,756,506 A | 5/1998 | Copeland et al. |
| 5,843,930 A * | 12/1998 | Purwar et al. .................. 514/171 |
| 5,912,255 A | 6/1999 | Bussell |
| 6,017,912 A | 1/2000 | Bussell |
| 6,869,965 B2 | 3/2005 | Gordeev et al. |
| 2004/0048786 A1 | 3/2004 | Vogt et al. |
| 2004/0137065 A1 | 7/2004 | Vogt et al. |

FOREIGN PATENT DOCUMENTS

| | | |
|---|---|---|
| BE | 870576 A | 3/1979 |
| BE | 887574 A | 6/1981 |
| DE | 3142854 A1 | 10/1981 |
| EP | 078362 B1 | 7/1982 |
| EP | 047005 B1 | 11/1984 |
| EP | 140116 B1 | 5/1988 |
| EP | 131839 B1 | 2/1989 |
| EP | 154780 B1 | 4/1990 |
| EP | 221463 B1 | 8/1991 |
| EP | 520240 A1 | 6/1992 |
| EP | 206283 B1 | 1/1993 |
| EP | 310849 B1 | 3/1993 |
| WO | WO 97/23217 | 7/1997 |
| WO | WO 2004/035071 | 4/2004 |

OTHER PUBLICATIONS

Cornick et al. "Streptococcus pnuemoniae: the evolution of antimicrobial resistance to beta-lactams, fluoroquinolones and macrolides". Microbes and Infection, 14 (2012) 573-583.*
Falagas et al. "Systematic review: fluoroquinolones for the treatment of intra-abdominal surgical infections". Alimentary Pharmacology and Therapeutics, 25, 123-131, 2007.*
Bakken JS. "The Fluoroquinolones: How Long Will Their Utility Last?". Scand J Infect Dis. 36: 85-92, 2004.*
H. R. Park et al., *Bull. Korean Chem. Soc.* vol. 21, No. 9, 2000, pp. 849-854.
S. Lecomte et al., *Effect of Magnesium Complexation by Fluoroquinolones on Their Antibacterial Properties*, Antimicrobial Agents and Chemotherapy, 38:12, 2810-2816, Dec. 1994.
B. Macias, et al., *Complexes of Co(II) and Zn(II) with Oflaxacin, Crystal Structure of $[Co(oflo)_2 (MeOH)_2]_{1-} 4H_2O$*, J. Pharm. Sci., 91:11, 2416-2423, Nov. 2000.
V. Loganathan et al., *In-vitro and In-vivo Drug-Drug Interaction Between Ciprofloxacin and Antacids*, The Eastern Pharmacist, Jun. 1966, 119-121.
A. Okhamafe et al., *Pharmacokinetic Interactions of Norfloxacin with Some Metallic Medicinal Agents*, International Journal of Pharmaceutics, 68, (1991), 11-18.
B. Lomaestro et al., *Quinolone-Antibiotic Interactions: A Review*, DICP, The Annals of Pharmacotherapy, 25, Nov. 1991, 1249-1258.
S. Primozic et al., *Transport Kinetics of Zinc-Ciprofloxacin Complex Across the Model Lipid Membrane*, Farm Vestn, 1999, 50, 294-295.
M. Zupancic et al., *Synthesis and Characterization of Two Novel Zinc (II) Complexes With Ciprofloxacin. Crystal Structure of $[C_{17}H_{19}N_3O_3FL]_2 \$ ZnCl_4 \$2H_2O$*, Croatia Chemica Acta, 74(1), 61-74, 2001.

(Continued)

*Primary Examiner* — Renee Claytor
(74) *Attorney, Agent, or Firm* — Haynes and Boone, LLP

(57) ABSTRACT

The invention relates to pharmaceutical compositions comprising (i) a fluoroquinolone, (ii) a salt formed between a carboxylate anion and a divalent metal cation, (iii) a liquid comprising an organic solvent selected from the group consisting of glycerol, propylene glycol, glycerol formal, and (iv) optionally water. The invention further relates to methods of treating or preventing a condition in an animal comprising administering to the animal in need thereof a pharmaceutical composition of the invention.

44 Claims, 8 Drawing Sheets

(56) References Cited

OTHER PUBLICATIONS

F. Kozjec et al., *Pharmacokinetics of Ciprofloxacin Metal Complexes*, Acta. Pharm., 46, 109-114, 1996.

V. Snaz-Nebot et al., *Acid Base Behavior of Quinolones in Aqueous Acetonitrile Mixtures*, Acta. Chemica. Scandinavica, 1997: 51: 896-903.

Y. Mizuki, et al. Pharmacokinetic Interactions Related to the Chemical Structure of Fluoroquinolones, *J. Antimicrobial Chemotherapy*, (1996) 37, Suppl. A 41-55.

*The Quinolones*, edited by V. Andriole, Academic Press, San Diego, 1988, pp. 44-53.

K. Timmers et al., *Ionization and Divalent Cation Dissociation Constants of Nalidixic and Oxolinic Acids*, Bioinorganic Chemistry, 9: 145-155 (1978).

L. Martinez et al., *Effect of Magnesium and Calcium Complexation on the Photochemical Properties of Norfloxacin*, Photochemistry and Photobiology, 1996, 64(6): 911-917.

G. Palu, et al., *Quinolone Binding to DNA is Mediated by Magnesium Ions*, Proc. Natl. Acad. Sci. USA, vol. 89, pp. 9671-9675, Oct. 1992.

S. Bazile-Pham Khac et al., *Interactions Between Fluoroquinolones, Mg+2, DNA and DNA Gyrase, Studies by Phase Partitioning in an Aqueous Two-Phase System by Affinity Chromatography*, J. Chromatography A, 668 (1994) 241-247.

J. Ferguson, *Fluoroquinolone Photosensitization: A Review of Clinical and Laboratory Studies*, Photochemistry and Photobiology, vol. 62, No. 6, pp. 954-958, 1995.

J. P. Slater et al. *Zinc in DNA Polymerases*, Biochemical and Biophysical Research Communications, vol. 44, No. 1, 1971.

C. F. Springate et al., *Escheria coli Deoxyribonucleic Acid Polymerase I, a Zinc Metalloenzyme, Nuclear Quadrapole Relaxation Studies of the Role of Bound Zin*, J. Biological Chemistry, vol. 218, No. 17, Sep. 10, 1973, pp. 5987-5903.

P. Valenzuela et al., *Are All Nucleotidyl Transferases Metalloenzymes?*, Biochemical and Biophysical Research Communications, vol. 53, No. 3, pp. 1036-1041, 1973.

Supplementary European Search Report, Mailed Dec. 17, 2012.

\* cited by examiner

FLUOROQUINOLONE COMPOSITIONS

CROSS REFERENCE TO RELATED APPLICATIONS

This application is a continuation of U.S. application Ser. No. 11/356,206, filed Feb. 17, 2006, the contents of which are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The present invention relates to pharmaceutical compositions comprising (i) a fluoroquinolone, (ii) a salt formed between a carboxylate anion and a divalent metal cation, and (iii) a liquid comprising (a) an organic solvent selected from the group consisting of glycerol, propylene glycol, glycerol formal, and mixtures thereof and (b) optionally water. The invention further relates to methods of treating or preventing a condition in an animal comprising administering to the animal in need thereof a pharmaceutical composition of the invention.

BACKGROUND OF THE INVENTION

The following discussion of the background of the invention is merely provided to aid the reader in understanding the invention and is not admitted to describe or constitute prior art to the present invention.

Fluoroquinolones are antibiotics used to treat infections caused by microorganisms. Fluoroquinolones have the basic structure shown below:

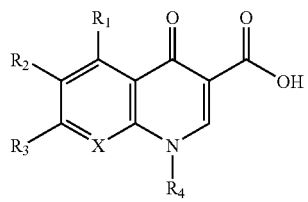

wherein $R_1$, $R_2$, $R_3$, and $R_4$ can be a variety of functional groups and X can be carbon or a variety of heteroatoms either of which may be substituted or unsubstituted.

Fluoroquinolones were first developed in the early 1960s. The first fluoroquinolone, nalidixic acid, was approved by the FDA in 1963 for the treatment of urinary tract infections. Nalidixic acid is rapidly absorbed after oral administration and is excreted into the urine in bactericidal concentrations. Nalidixic acid, however, has several limitations that prevents its use in other types of infections. Specifically, nalidixic acid has a narrow spectrum of activity and microorganisms easily developed resistance to the drug. The development of other fluoroquinolones by chemically altering the basic structure of nalidixic acid, however, has led to improved fluoroquinolones that are more effective against resistant bacteria and effective against a broader range of bacteria.

Representative fluoroquinolones include but are not limited to those described in BE 870,576, U.S. Pat. No. 4,448,962, DE 3,142,854, EP 047,005, EP 206,283, BE 887,574, EP 221,463, EP 140,116, EP 131,839, EP 154,780, EP 078,362, EP 310,849, EP 520,240, U.S. Pat. Nos. 4,499,091, 4,704,459, 4,795,751, 4,668,784, and 5,532,239.

The fluoroquinolone class of antibiotics are a powerful tool in combating bacterial infections. Fluoroquinolones have been used extensively to treat respiratory tract infections (including for example, bronchitis, pneumonia, tuberculosis), urinary tract infections, diarrhea, postoperative-wound infections, bone and joint infections, skin infections, inflammation of the prostate, ear infections, various sexually transmitted diseases, various infections that affect people with AIDS, and other conditions, in animals and humans. Fluoroquinolones are active against a wide spectrum of gram-positive and gram-negative bacteria. For example, various fluoroquinolones have been found to be effective against *Staphylococcus aureus*, *Streptococcus pneumoniae*, coagulese-negative staphylococci, *Streptococcus pyogenes*, *Staphylococcus epidermis*, *Pseudomonas aeruginosa*, *Escherichia coli*, *Klebsiella pneumoniae*, *Enterobacter cloacae*, *Proteus mirabilis*, *Proteus vulgaris*, *Providencia stuartii*, *Morganella morganii*, *Citrobacter diversus*, *Citrobacter freundii*, *Haemophilus influenzae*, and *Neisseria gonorrhea*, and other organisms. Indeed, the mounting resistance of *Staphylococcus aureus* to both penicillin and erythromycin has made the fluoroquinolone antibiotics a viable alternative for the treatment of skin diseases.

The mode of action of fluoroquinolones is to target DNA gyrase in the bacteria and interfere with bacterial replication.

Fluoroquinolones can be administered orally, topically, or parenterally.

U.S. Pat. No. 5,476,854 describes the oral, intravenous, and transdermal use of lomefloxacin to treat urinary tract infections, upper respiratory tract infections, sexually-transmitted infections, opthalmological infections, and intestinal infections.

U.S. Pat. No. 6,017,912 discloses a method of topically treating bacterial infections of the skin caused by susceptible organisms that comprises administering to an individual a composition of a fluoroquinolone antibiotic in a vehicle containing acetone and alcohol, applied directly to the affected areas of the human skin.

U.S. Pat. No. 5,912,255 discloses a pharmaceutical composition comprising a fluoroquinolone and benzoyl peroxide in a vehicle. The compositions are useful for the topical treatment of a variety of skin conditions.

U.S. Pat. No. 5,756,506 discloses a method of treating animals with fluoroquinolones by administering to the animal a single high dose of the fluoroquinolone to replace multiple lower doses.

U.S. Pat. No. 5,532,239 discloses treating nephrotic syndromes with fluoroquinolone derivatives.

Divalent cations are known to reduce the absorption and/or bioavailability of fluoroquinolones. See, for example, S. Lecomte et al., *Effect of Magnesium Complexation by Fluoroquinolones on Their Antibacterial Properties*, Antimicrobial Agents and Chemotherapy, 38:12, 2810-2816, December 1994; Hyoung-Ryun Park, et al., *Ionization and Divalent Cation Complexation of Quinolone Antibiotics in Aqueous Solution*, Bull. Korean Chem. Soc. 2000, 21:9, 849-854; B. Macias, et al., *Complexes of Co(II) and Zn(II) with Oflaxacin, Crystal Structure of [Co(oflo)$_2$(MeOH)$_2$]$4H_2O$*, J. Pharm. Sci., 91:11, 2416-2423, November 2000; V. Loganathan et al., *In-vitro and In-vivo Drug-Drug Interaction Between Ciprofloxacin and Antacids*, The Eastern Pharmacist, June 1966, 119-121; A. Okhamafe et al., *Pharmacokinetic Interactions of Norfloxacin with Some Metallic Medicinal Agents*, International Journal of Pharmaceutics, 68, (1991), 11-18; B. Lomaestro et al., *Quinolone-Antibiotic Interactions: A Review*, DICP, The Annals of Pharmacotherapy, 25, November 1991, 1249-1258; S. Primozic et al., *Transport Kinetics of Zinc-Ciprofloxacin Complex Across the Model Lipid Membrane*, Farm Vestn, 1999, 50, 294-295; M. Zupancic et al., *Synthesis and Characterization of Two Novel Zinc (II) Complexes With Ciprofloxacin. Crystal Structure of $[C_{17}H_{19}N_3O_3F]_2\$ZnCl_4\$2H_2O$*, Croatia Chemica Acta, 74(1), 61-74, 2001; and F. Kozjec et al., *Pharmacokinetics of Ciprofloxacin Metal Complexes*, Acta. Pharm., 46, 109-114, 1996).

Solid oral pharmaceutical compositions, such as tablets and capsules, can be difficult for some individuals to swallow. For example, pediatric patients often find it difficult to swallow solid oral pharmaceutical compositions. Furthermore, solid oral pharmaceutical compositions can be difficult to administer to animals, such as cats. Thus, in many instances, liquid oral pharmaceutical compositions, such as solutions and suspensions, are desirable because they are easier to administer. Fluoroquinolones, however, are difficult to dissolve in liquids. Accordingly, there is a need in the art for new liquid fluoroquinolone compositions that can be more easily administered to animals.

Citation of any reference in this section of this application is not to be construed that such reference is prior art to the present application.

SUMMARY OF THE INVENTION

The invention relates to pharmaceutical compositions comprising (i) a fluoroquinolone, (ii) a salt formed between a carboxylate anion and a divalent metal cation, and (iii) a liquid comprising (a) an organic solvent selected from the group consisting of glycerol, propylene glycol, glycerol formal, and mixtures thereof and (b) optionally water.

The invention further relates to a pharmaceutical composition comprising a complex of formula:

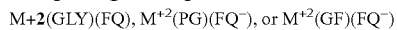

M+2(GLY)(FQ), M$^{+2}$(PG)(FQ$^-$), or M$^{+2}$(GF)(FQ$^-$)

wherein:
FQ is a fluoroquinolone or an anion of a fluoroquinolone,
M$^{+2}$ is a divalent metal cation,
GLY is glycerol or an anion of glycerol,
PG is propylene glycol or an anion of propylene glycol; and
GF is glycerol formal or an anion of glycerol formal.

The invention further relates to a pharmaceutical composition comprising:
(i) a fluoroquinolone;
(ii) a salt formed between a carboxylate anion and a divalent metal cation; and
(iii) a liquid comprising an organic solvent and water,
wherein the pharmaceutical composition is a solution of the fluoroquinolone in the liquid and the concentration of the fluoroquinolone in the solution is higher than can be obtained in the absence of the organic solvent.

The invention further relates to methods of treating or preventing a condition in an animal comprising administering to the animal in need thereof a pharmaceutical composition of the invention. The pharmaceutical compositions of the invention, being a liquid, are in many instances easier to administer than solid oral dosage forms.

DETAILED DESCRIPTION OF THE INVENTION

Figure 1:
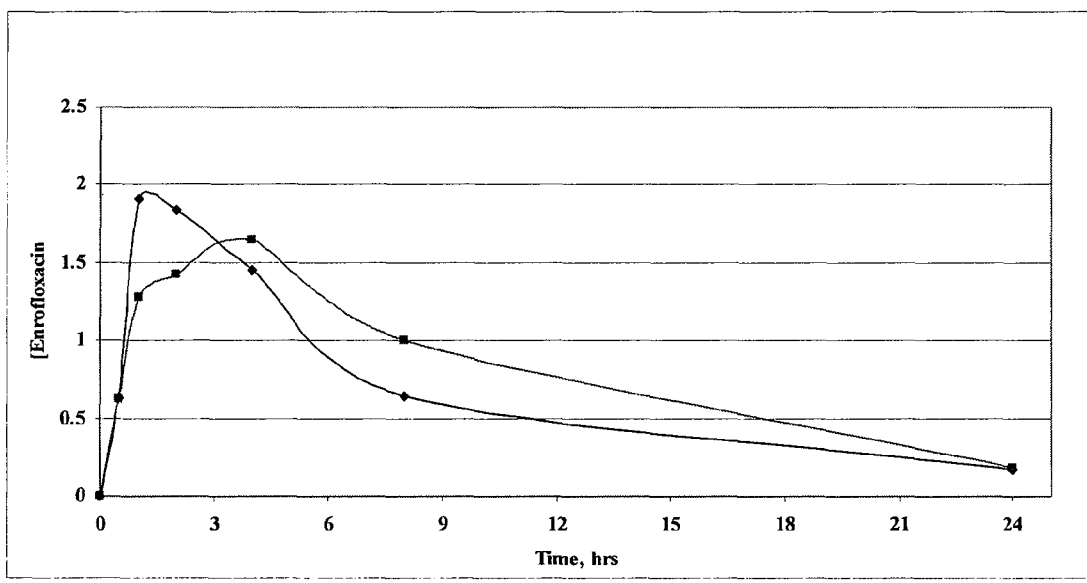
FIG. 1 is a graphical representation of the concentration of enrofloxacin in serum in µg/mL as a function of time (hours) when enrofloxacin is orally administered to a dog. The symbol (■) represents data points for administration of three tablets (22.7 mg each, total 68 mg) of commercially available enrofloxacin (Baytril®, commercially available from Bayer Health Care of Shawnee Mission, Kans.) and the symbol (♦) represents data points for administration of enrofloxacin as an oral liquid pharmaceutical formulation of the invention at a dose of 68 mg (i.e., 3 mL of a liquid composition of the invention having an enrofloxacin concentration of 23 mg/mL).

The invention relates to pharmaceutical compositions comprising (i) a fluoroquinolone, (ii) a salt formed between a carboxylate anion and a divalent metal cation, and (iii) a liquid comprising (a) an organic solvent selected from the group consisting of glycerol, propylene glycol, glycerol formal, and mixtures thereof and (b) optionally water. The invention further relates to methods of treating or preventing a condition in an animal comprising administering to the animal in need thereof a pharmaceutical composition of the invention.

Definitions

The term "fluoroquinolone," as used herein, means any compound having the basic structure:

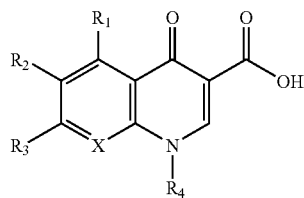

wherein $R_1$, $R_2$, $R_3$, and $R_4$ can be a variety of functional groups and X can be carbon, which may be substituted or unsubstituted, or nitrogen. One skilled in the art would readily recognize fluoroquinolones useful in the compositions and methods of the invention. Typically, the fluoroquinolones are useful as antibiotics but they may also be used to treat other conditions (for example, nephrotic syndromes).

The term "salt," as used herein, means two compounds that are not covalently bound but are chemically bound by ionic interactions. Accordingly, in a salt formed between a carboxylate anion and a divalent metal cation, the carboxylate anion and a divalent metal cation are chemically bound by ionic interactions.

The term "divalent metal cation," as used herein means a metal ion in the +2 oxidation state. Representative divalent cations include, but are not limited to, divalent cations of the alkaline earth metals (i.e., $Be^{+2}$, $Mg^{+2}$, $Ca^{+2}$, $Sr^{+2}$, $Ba^{+2}$, and $Ra^{+2}$), $Cu^{+2}$, $Fe^{+2}$, and $Zn^{+}$.

The term "carboxylate anion," as that term is used herein, means the anionic form of a carboxylic acid, i.e., R—COO—, wherein R can be an optionally substituted phenyl or an optionally substituted $C_1$ to $C_6$ saturated or unsaturated, straight chain or branched alkyl group. Suitable substituents include, but are not limited to, —$N(R_1)_2$, $SR_1$, —$COOR_2$, —Cl, —Br, —I, —F, —$OR_1$, wherein each $R_1$ is independently H or a $C_1$ to $C_6$ saturated or unsaturated, straight chain or branched alkyl group and each $R_2$ is a $C_1$ to $C_6$ saturated or unsaturated, straight chain or branched alkyl group.

Since the carboxylate anion is typically a mono anion, i.e., has a single carboxylate functional group, and the metal cation is a divalent metal cation, the carboxylate salt of a divalent metal cation includes two equivalents of carboxylate anion for each equivalent of divalent metal cation. Accordingly, the carboxylate salt of a divalent metal cation typically has the structure (R—$COO^-)_2 M^{+2}$, wherein $M^{+2}$ is the divalent metal cation.

The term "glycerol," as that term is used herein, means $CH_2(OH)CH(OH)CH_2(OH)$.

The term "propylene glycol," as that term is used herein, means $CH_2(OH)CH_2CH_2(OH)$ or $CH_2(OH)CH_2(OH)CH_3$, i.e., 1,3-propylene glycol or 1,2-propylene glycol.

The term "glycerol formal," as used herein means an organic solvent of formula $C_4H_8O_3$ that exists as a mixture of 5-hydroxy-1,3-dioxane and 4-hydroxymethyl-1,3-dioxolane in a ratio of about 60:40. Although the solvent glycerol formal consists of two chemical compounds, the two chemical compounds being in a specific ratio of about 60:40, it is typically considered a "solvent" rather than a mixture of compounds. This is because the 5-hydroxy-1,3-dioxane and 4-hydroxymethyl-1,3-dioxolane are in equilibrium with each other. Accordingly, the term glycerol formal (i.e., a mixture of 5-hydroxy-1,3-dioxane and 4-hydroxymethyl-1,3-dioxolane in a ratio of about 60:40), as used herein, is an organic solvent.

The term "solution," as used herein, means a uniformly dispersed mixture at the molecular or ionic level of one or more solid or liquid substances (solute) in one or more other liquid substances (solvent).

The phrase "injectable" or "injectable composition," as used herein, means a composition that can be drawn into a syringe and injected subcutaneously, intraperitoneally, or intramuscularly into an animal without causing adverse effects due to the presence of solid material in the composition. Solid materials include, but are not limited to, crystals, gummy masses, and gels. Typically, a formulation or composition is considered to be injectable when no more than about 15%, preferably no more than about 10%, more preferably no more than about 5%, even more preferably no more than about 2%, and most preferably no more than about 1% of the formulation is retained on a 0.22 µm filter when the formulation is filtered through the filter at room temperature, i.e., about 22° C.

The phrase "substantially free of," as used herein, means less than about 2 percent by weight. For example, the phrase "a liquid substantially free of water" means that the amount of water in the liquid is less than about 2 percent by volume of the liquid.

The phrase "treating," "treatment of," and the like includes the amelioration or cessation of a specified condition.

The phrase "preventing," "prevention of," and the like include the avoidance of the onset of a condition.

The term "animal," as used herein, includes, but is not limited to, humans, canines, felines, equines, bovines, ovines, porcines, amphibians, reptiles, and avians. Representative animals include, but are not limited to a cow, a horse, a sheep, a pig, an ungulate, a chimpanzee, a monkey, a baboon, a chicken, a turkey, a mouse, a rabbit, a rat, a guinea pig, a dog, a cat, and a human. In one embodiment, the animal is a canine, a feline, an equine, a bovine, an ovine, or a porcine.

The term "condition," as used herein means an interruption, cessation, or disorder of a bodily function, system, or organ. Representative conditions include, but are not limited to, bacterial infections and nephrotic syndromes (such as those disclosed in U.S. Pat. No. 5,532,239, the contents of which are expressly incorporated herein by reference thereto).

The term "effective amount," as used herein, means an amount sufficient to treat or prevent a condition in an animal.

The term "about," as used herein to describe a range of values, applies to both the upper limit and the lower limit of the range. For example, the phrase "ranges from about 90:10 to 10:90" has the same meaning as "ranges from about 90:10 to about 10:90."

The Pharmaceutical Compositions

The pharmaceutical compositions comprise (i) a fluoroquinolone, (ii) a salt formed between a carboxylate anion and a divalent metal cation, and (iii) a liquid comprising (a) an organic solvent selected from the group consisting of glycerol, propylene glycol, glycerol formal, and mixtures thereof and (b) optionally water.

In one embodiment, the pharmaceutical composition is a solution.

In one embodiment, the pharmaceutical composition is injectable.

The fluoroquinolone can be any fluoroquinolone known to those skilled in the art. Representative fluoroquinolones useful in the compositions and methods of the invention include, but are not limited to, those described in BE 870,576, U.S. Pat. No. 4,448,962, DE 3,142,854, EP 047,005, EP 206,283, BE 887,574, EP 221,463, EP 140,116, EP 131,839, EP 154,780, EP 078,362, EP 310,849, EP 520,240, U.S. Pat. Nos. 4,499,091, 4,704,459, 4,795,751, 4,668,784, and 5,532,239, the contents of which are expressly incorporated herein by reference thereto.

Representative fluoroquinolones useful in the compositions and methods of the invention include, but are not limited to, ciprofloxacin (commercially available as Cipro®), enrofloxacin (commercially available as Baytril®), enoxacin (commercially available as Penetrex®), gatifloxacin (commercially available as Tequin®), gemifloxacin (commercially available as Factive®), levofloxacin (commercially available as Levaquin®), lomefloxacin (commercially available as Maxaquin®), moxifloxacin (commercially available as Avelox®), norfloxacin (commercially available as Noroxin®), ofloxacin (commercially available as Floxin®), sparfloxacin (commercially available as Zagam®), trovafloxacin (commercially available as Trovan®), difloxacin, cinofloxacin, pefloxacin, tosufloxacin, temafloxacin, fleroxacin, amifloxacin, binfloxacin, danofloxacin, marbofloxacin, ruflocaxin, and sarafloxacin.

In one embodiment, the fluoroquinolone is ciprofloxacin.
In one embodiment, the fluoroquinolone is enrofloxacin.
In one embodiment, the fluoroquinolone is gatifloxacin.
In one embodiment, the fluoroquinolone is gemifloxacin.
In one embodiment, the fluoroquinolone is levofloxacin.
In one embodiment, the fluoroquinolone is lomefloxacin.
In one embodiment, the fluoroquinolone is moxifloxacin.
In one embodiment, the fluoroquinolone is ofloxacin.
In one embodiment, the fluoroquinolone is sparfloxacin.
In one embodiment, the fluoroquinolone is trovafloxacin.
In one embodiment, the fluoroquinolone is difloxacin.
In one embodiment, the fluoroquinolone is cinofloxacin.
In one embodiment, the fluoroquinolone is pefloxacin.
In one embodiment, the fluoroquinolone is tosufloxacin.
In one embodiment, the fluoroquinolone is temafloxacin.
In one embodiment, the fluoroquinolone is fleroxacin.
In one embodiment, the fluoroquinolone is amifloxacin.
In one embodiment, the fluoroquinolone is binfloxacin.
In one embodiment, the fluoroquinolone is danofloxacin.
In one embodiment, the fluoroquinolone is marbofloxacin.
In one embodiment, the fluoroquinolone is ruflocaxin.
In one embodiment, the fluoroquinolone is sarafloxacin.

In one embodiment, the divalent metal cation is a divalent metal cation of an alkaline earth metal.

In one embodiment, the divalent metal cation is $Mg^{+2}$. $Mg^{+2}$ is a preferred divalent metal cation.

In one embodiment, the divalent metal cation is $Zn^{+2}$. $Zn^{+2}$ is a preferred divalent metal cation.

In one embodiment, the divalent metal cation is $Ca^{+2}$.
In one embodiment, the divalent metal cation is $Cu^{+2}$.
In one embodiment, the divalent metal cation is $Fe^{+2}$.

In one embodiment, the carboxylate anion is a substituted benzoate anion.

In one embodiment, the carboxylate anion is a benzoate anion.

In one embodiment, the carboxylate anion is an optionally substituted $C_1$ to $C_6$ saturated or unsaturated, straight chain or branched alkyl group.

In one embodiment, the carboxylate anion is an unsubstituted $C_1$ to $C_6$ saturated or unsaturated, straight chain or branched alkyl group.

In one embodiment, the carboxylate anion is an unsubstituted $C_1$ to $C_6$ saturated straight chain or branched alkyl group.

In one embodiment, the carboxylate anion is an unsubstituted $C_1$ to $C_6$ saturated straight chain alkyl group.

In one embodiment, the carboxylate anion is acetate anion.
In one embodiment, the salt formed between a carboxylate anion and a divalent metal cation is zinc acetate.
In one embodiment, the salt formed between a carboxylate anion and a divalent metal cation is magnesium acetate.

When the liquid includes water, the water is typically present in an amount up to about 90 percent (v/v) of the liquid. In one embodiment, the water is present in an amount up to about 75 percent (v/v) of the liquid. In one embodiment, the water is present in an amount up to about 50 percent (v/v) of the liquid. In one embodiment, the water is present in an amount up to about 25 percent (v/v) of the liquid. In one embodiment, the water is present in an amount up to about 20 percent (v/v) of the liquid. In one embodiment, the water is present in an amount up to about 10 percent (v/v) of the liquid.

In one embodiment, the liquid is substantially free of water. In one embodiment, the liquid contains less than about 1 percent by volume of water. In one embodiment, the liquid contains less about 0.5 percent by volume of water. In one embodiment, the liquid contains less about 0.2 percent by volume of water. Pharmaceutically compositions that are substantially free of water are advantageous since they are not conducive to bacterial growth. Accordingly, it is typically not necessary to include a preservative in pharmaceutical compositions that are substantially free of water.

In one embodiment, the organic solvent comprises glycerol.

In one embodiment, the organic solvent comprises propylene glycol. In one embodiment, the propylene glycol is 1,3-propylene glycol. In one embodiment, the propylene glycol is 1,2-propylene glycol.

In one embodiment, the solvent comprises glycerol formal.
In one embodiment, the solvent comprises a mixture of glycerol and propylene glycol.
In one embodiment, the solvent comprises a mixture of glycerol and glycerol formal.
In one embodiment, the solvent comprises a mixture of propylene glycol and glycerol formal.
In one embodiment, the solvent comprises a mixture of propylene glycol, glycerol, and glycerol formal.
In one embodiment, the organic solvent comprises a mixture of glycerol and water.
In one embodiment, the organic solvent comprises a mixture of propylene glycol and water. In one embodiment, the propylene glycol is 1,3-propylene glycol. In one embodiment, the propylene glycol is 1,2-propylene glycol.
In one embodiment, the solvent comprises a mixture of glycerol formal and water.
In one embodiment, the solvent comprises a mixture of glycerol, propylene glycol, and water.
In one embodiment, the solvent comprises a mixture of glycerol, glycerol formal, and water.
In one embodiment, the solvent comprises a mixture of propylene glycol, glycerol formal, and water.
In one embodiment, the solvent comprises a mixture of propylene glycol, glycerol, glycerol formal, and water.
In one embodiment, the organic solvent is glycerol.

In one embodiment, the organic solvent is propylene glycol. In one embodiment, the propylene glycol is 1,3-propylene glycol. In one embodiment, the propylene glycol is 1,2-propylene glycol.

In one embodiment, the solvent is glycerol formal.

In one embodiment, the solvent is a mixture of glycerol and propylene glycol.

In one embodiment, the solvent is a mixture of glycerol and glycerol formal.

In one embodiment, the solvent is a mixture of propylene glycol and glycerol formal.

In one embodiment, the solvent is a mixture of propylene glycol, glycerol, and glycerol formal.

In one embodiment, the organic solvent is a mixture of glycerol and water.

In one embodiment, the organic solvent is a mixture of propylene glycol and water. In one embodiment, the propylene glycol is 1,3-propylene glycol. In one embodiment, the propylene glycol is 1,2-propylene glycol.

In one embodiment, the solvent is a mixture of glycerol formal and water.

In one embodiment, the solvent is a mixture of glycerol, propylene glycol, and water.

In one embodiment, the solvent is a mixture of glycerol and glycerol formal, and water.

In one embodiment, the solvent is a mixture of propylene glycol, glycerol formal, and water.

In one embodiment, the solvent is a mixture of propylene glycol, glycerol, glycerol formal, and water.

In one embodiment, the liquid comprises glycerol in an amount ranging from about 25 percent to 100 percent by volume of the liquid.

In one embodiment, the liquid comprises glycerol in an amount ranging from about 50 percent to 90 percent by volume of the liquid.

In one embodiment, the liquid comprises glycerol in an amount ranging from about 60 percent to 80 percent by volume of the liquid.

In one embodiment, the liquid comprises glycerol in an amount ranging from about 75 percent to 80 percent by volume of the liquid.

In one embodiment, the liquid comprises propylene glycol in an amount ranging from about 25 percent to 100 percent by volume of the liquid.

In one embodiment, the liquid comprises propylene glycol in an amount ranging from about 50 percent to 90 percent by volume of the liquid.

In one embodiment, the liquid comprises propylene glycol in an amount ranging from about 60 percent to 80 percent by volume of the liquid.

In one embodiment, the liquid comprises propylene glycol in an amount ranging from about 75 percent to 80 percent by volume of the liquid.

In one embodiment, the liquid comprises glycerol formal in an amount ranging from about 25 percent to 100 percent by volume of the liquid.

In one embodiment, the liquid comprises glycerol formal in an amount ranging from about 50 percent to 90 percent by volume of the liquid.

In one embodiment, the liquid comprises glycerol formal in an amount ranging from about 60 percent to 80 percent by volume of the liquid.

In one embodiment, the liquid comprises glycerol formal in an amount ranging from about 75 percent to 80 percent by volume of the liquid.

In one embodiment, the liquid comprises a mixture of glycerol and propylene glycol; glycerol and glycerol formal; propylene glycol and glycerol formal; or glycerol, propylene glycol, and glycerol formal in an amount ranging from about 25 percent to 100 percent by volume of the liquid.

In one embodiment, the liquid comprises a mixture of glycerol and propylene glycol; glycerol and glycerol formal; propylene glycol and glycerol formal; or glycerol, propylene glycol, and glycerol formal in an amount ranging from about 50 percent to 90 percent by volume of the liquid.

In one embodiment, the liquid comprises a mixture of glycerol and propylene glycol; glycerol and glycerol formal; propylene glycol and glycerol formal; or glycerol, propylene glycol, and glycerol formal in an amount ranging from about 60 percent to 80 percent by volume of the liquid.

In one embodiment, the liquid comprises a mixture of glycerol and propylene glycol; glycerol and glycerol formal; propylene glycol and glycerol formal; or glycerol, propylene glycol, and glycerol formal in an amount ranging from about 75 percent to 80 percent by volume of the liquid.

In one embodiment, the liquid comprises glycerol in an amount ranging from about 25 percent to 100 percent by volume of the liquid and water in an amount ranging from about 75 percent to 0 percent by volume of the liquid.

In one embodiment, the liquid comprises glycerol in an amount ranging from about 50 percent to 90 percent by volume of the liquid and water in an amount ranging from about 50 percent to 10 percent by volume of the liquid.

In one embodiment, the liquid comprises glycerol in an amount ranging from about 60 percent to 80 percent by volume of the liquid and water in an amount ranging from about 40 percent to 20 percent by volume of the liquid.

In one embodiment, the liquid comprises glycerol in an amount ranging from about 75 percent to 80 percent by volume of the liquid and water in an amount ranging from about 25 percent to 20 percent by volume of the liquid.

In one embodiment, the liquid comprises propylene glycol in an amount ranging from about 25 percent to 100 percent by volume of the liquid and water in an amount ranging from about 75 percent to 0 percent by volume of the liquid.

In one embodiment, the liquid comprises propylene glycol in an amount ranging from about 50 percent to 90 percent by volume of the liquid and water in an amount ranging from about 50 percent to 10 percent by volume of the liquid.

In one embodiment, the liquid comprises propylene glycol in an amount ranging from about 60 percent to 80 percent by volume of the liquid and water in an amount ranging from about 40 percent to 20 percent by volume of the liquid.

In one embodiment, the liquid comprises propylene glycol in an amount ranging from about 75 percent to 80 percent by volume of the liquid and water in an amount ranging from about 25 percent to 20 percent by volume of the liquid.

In one embodiment, the liquid comprises glycerol formal in an amount ranging from about 25 percent to 100 percent by volume of the liquid and water in an amount ranging from about 75 percent to 0 percent by volume of the liquid.

In one embodiment, the liquid comprises glycerol formal in an amount ranging from about 50 percent to 90 percent by volume of the liquid and water in an amount ranging from about 50 percent to 10 percent by volume of the liquid.

In one embodiment, the liquid comprises glycerol formal in an amount ranging from about 60 percent to 80 percent by volume of the liquid and water in an amount ranging from about 40 percent to 20 percent by volume of the liquid.

In one embodiment, the liquid comprises glycerol formal in an amount ranging from about 75 percent to 80 percent by volume of the liquid and water in an amount ranging from about 25 percent to 20 percent by volume of the liquid.

In one embodiment, the liquid comprises glycerol in an amount ranging from about 25 percent to 100 percent by volume of the liquid and propylene glycol in an amount ranging from about 75 percent to 0 percent by volume of the liquid.

In one embodiment, the liquid comprises glycerol in an amount ranging from about 50 percent to 90 percent by volume of the liquid and propylene glycol in an amount ranging from about 50 percent to 10 percent by volume of the liquid.

In one embodiment, the liquid comprises glycerol in an amount ranging from about 60 percent to 80 percent by volume of the liquid and propylene glycol in an amount ranging from about 40 percent to 20 percent by volume of the liquid.

In one embodiment, the liquid comprises glycerol in an amount ranging from about 75 percent to 80 percent by volume of the liquid and propylene glycol in an amount ranging from about 25 percent to 20 percent by volume of the liquid.

In one embodiment, the liquid comprises glycerol in an amount ranging from about 25 percent to 100 percent by volume of the liquid and glycerol formal in an amount ranging from about 75 percent to 0 percent by volume of the liquid.

In one embodiment, the liquid comprises glycerol in an amount ranging from about 50 percent to 90 percent by volume of the liquid and glycerol formal in an amount ranging from about 50 percent to 10 percent by volume of the liquid.

In one embodiment, the liquid comprises glycerol in an amount ranging from about 60 percent to 80 percent by volume of the liquid and glycerol formal in an amount ranging from about 40 percent to 20 percent by volume of the liquid.

In one embodiment, the liquid comprises glycerol in an amount ranging from about 75 percent to 80 percent by volume of the liquid and glycerol formal in an amount ranging from about 25 percent to 20 percent by volume of the liquid.

In one embodiment, the liquid comprises propylene glycol in an amount ranging from about 25 percent to 100 percent by volume of the liquid and glycerol in an amount ranging from about 75 percent to 0 percent by volume of the liquid.

In one embodiment, the liquid comprises propylene glycol in an amount ranging from about 50 percent to 90 percent by volume of the liquid and glycerol in an amount ranging from about 50 percent to 10 percent by volume of the liquid.

In one embodiment, the liquid comprises propylene glycol in an amount ranging from about 60 percent to 80 percent by volume of the liquid and glycerol in an amount ranging from about 40 percent to 20 percent by volume of the liquid.

In one embodiment, the liquid comprises propylene glycol in an amount ranging from about 75 percent to 80 percent by volume of the liquid and glycerol in an amount ranging from about 25 percent to 20 percent by volume of the liquid.

In one embodiment, the liquid comprises propylene glycol in an amount ranging from about 25 percent to 100 percent by volume of the liquid and glycerol formal in an amount ranging from about 75 percent to 0 percent by volume of the liquid.

In one embodiment, the liquid comprises propylene glycol in an amount ranging from about 50 percent to 90 percent by volume of the liquid and glycerol formal in an amount ranging from about 50 percent to 10 percent by volume of the liquid.

In one embodiment, the liquid comprises propylene glycol in an amount ranging from about 60 percent to 80 percent by volume of the liquid and glycerol formal in an amount ranging from about 40 percent to 20 percent by volume of the liquid.

In one embodiment, the liquid comprises propylene glycol in an amount ranging from about 75 percent to 80 percent by volume of the liquid and glycerol formal in an amount ranging from about 25 percent to 20 percent by volume of the liquid.

In one embodiment, the liquid comprises glycerol formal in an amount ranging from about 25 percent to 100 percent by volume of the liquid and propylene glycol in an amount ranging from about 75 percent to 0 percent by volume of the liquid.

In one embodiment, the liquid comprises glycerol formal in an amount ranging from about 50 percent to 90 percent by volume of the liquid and propylene glycol in an amount ranging from about 50 percent to 10 percent by volume of the liquid.

In one embodiment, the liquid comprises glycerol formal in an amount ranging from about 60 percent to 80 percent by volume of the liquid and propylene glycol in an amount ranging from about 40 percent to 20 percent by volume of the liquid.

In one embodiment, the liquid comprises glycerol formal in an amount ranging from about 75 percent to 80 percent by volume of the liquid and propylene glycol in an amount ranging from about 25 percent to 20 percent by volume of the liquid.

In one embodiment, the liquid comprises glycerol formal in an amount ranging from about 25 percent to 100 percent by volume of the liquid and glycerol in an amount ranging from about 75 percent to 0 percent by volume of the liquid.

In one embodiment, the liquid comprises glycerol formal in an amount ranging from about 50 percent to 90 percent by volume of the liquid and glycerol in an amount ranging from about 50 percent to 10 percent by volume of the liquid.

In one embodiment, the liquid comprises glycerol formal in an amount ranging from about 60 percent to 80 percent by volume of the liquid and glycerol in an amount ranging from about 40 percent to 20 percent by volume of the liquid.

In one embodiment, the liquid comprises glycerol formal in an amount ranging from about 75 percent to 80 percent by volume of the liquid and glycerol in an amount ranging from about 25 percent to 20 percent by volume of the liquid.

Organic solvents other than glycerol, propylene glycol, and glycerol formal that can be used in the pharmaceutical compositions of the invention include $C_3$-$C_6$ alcohols.

In one embodiment, the $C_3$-$C_6$ alcohols have at least two hydroxyl groups. In one embodiment, the $C_3$-$C_6$ alcohol is a dihydroxy alcohol. In one embodiment, the $C_3$-$C_6$ alcohol is a trihydroxy alcohol.

Typically, the fluoroquinolone is present in the pharmaceutical composition in an amount ranging from about 2 percent to 20 percent by weight of the pharmaceutical composition. In one embodiment, the fluoroquinolone is present in the pharmaceutical composition in an amount ranging from about 3 percent to 20 percent by weight of the pharmaceutical composition. In one embodiment, the fluoroquinolone is present in the pharmaceutical composition in an amount ranging from about 5 percent to 20 percent by weight of the pharmaceutical composition. In one embodiment, the fluoroquinolone is present in the pharmaceutical composition in an amount ranging from about 10 percent to 20 percent by weight of the pharmaceutical composition. In one embodiment, the fluoroquinolone is present in the pharmaceutical composition in an amount ranging from about 15 percent to 20 percent by weight of the pharmaceutical composition. Preferably, the fluoroquinolone is present in the pharmaceutical composition without using excipients to improve the solubility. In one embodiment, the fluoroquinolone is present in the pharmaceutical composition in an amount ranging from about 2 percent to 15 percent by weight of the pharmaceutical composition. In one embodiment, the fluoroquinolone is present in the pharmaceutical composition in an amount ranging from about 2 percent to 10 percent by weight of the pharmaceutical composition. In one embodiment, the fluoroquinolone is present in the pharmaceutical composition in an amount ranging from about 2 percent to 5 percent by weight of the pharmaceutical composition. In one embodiment, the fluoroquinolone is present in the pharmaceutical composition in an amount ranging from about 5 percent to 15 percent by weight of the pharmaceutical composition. In one embodiment, the fluoroquinolone is present in the pharmaceutical composition in an amount ranging from about 5 percent to 10 percent by weight of the pharmaceutical composition.

In some embodiments, it is even possible that the fluoroquinolone is present in the pharmaceutical composition in an amount greater than about 20 percent by weight of the pharmaceutical composition. In one embodiment, the fluoroquinolone is present in the pharmaceutical composition in an amount greater than about 30 percent by weight of the pharmaceutical composition. In one embodiment, the fluoroquinolone is present in the pharmaceutical composition in an amount greater than about 35 percent by weight of the pharmaceutical composition. In one embodiment, the fluoroquinolone is present in the pharmaceutical composition in an amount of about 40 percent by weight of the pharmaceutical composition.

The ratio of the fluoroquinolone to the salt formed between a carboxylate anion and a divalent metal cation ranges from about 3 to 0.5. In one embodiment, the ratio of the fluoroquinolone to the salt formed between a carboxylate anion and a divalent metal cation ranges from about 2.5 to 0.8. In one embodiment, the ratio of the fluoroquinolone to the salt formed between a carboxylate anion and a divalent metal cation ranges from about 2.3 to 0.9. In one embodiment, the ratio of the fluoroquinolone to the salt formed between a carboxylate anion and a divalent metal cation ranges from about 2.1 to 1.

In one embodiment, the pharmaceutical composition is a solution.

In one embodiment, the pharmaceutical composition is injectable.

The pharmaceutical compositions of the invention can be a solution of the fluoroquinolone in the liquid, wherein the fluoroquinolone is present in a sufficiently high concentration to provide a pharmaceutical composition that is therapeutically useful. Typically, fluoroquinolones are not sufficiently soluble in water to provide pharmaceutical compositions that are solutions, wherein the fluoroquinolone is present in a sufficiently high concentration to be therapeutically useful. For example, enrofloxacin will not dissolve in water at a sufficient concentration to provide a therapeutically useful pharmaceutical composition. Similarly, salts formed between two fluoroquinolone molecules and a divalent metal ion, i.e. (fluoroquinolone)$_2$M$^{+2}$, such as those known in the art, are not sufficiently soluble in water to provide pharmaceutical compositions that are solutions. Salts formed between two fluoroquinolone molecules and a divalent metal ion, i.e. (FQ)$_2$M$^{+2}$, can be prepared according to the reaction shown below:

$$FQ + MO + HCl \rightarrow M[FQ]_2$$

wherein FQ is a fluoroquinolone or anion of fluoroquinolone. For examples of salts formed between two fluoroquinolone molecules and a divalent metal ion see, B. Macias, et al., *Complexes of Co(II) and Zn(II) with Ofloxacin, Crystal Structure of [Co(oflo)$_2$(MeOH)$_2$]$4H_2O*, J. Pharm. Sci., 91:11, 2416-2423, November 2000; M. Zupancic et al., *Synthesis and Characterization of Two Novel Zinc (II) Complexes With Ciprofloxacin. Crystal Structure of [C$_{17}$H$_{19}$N$_3$O$_3$F]$_2$$ZnCl$_4$$2H_2O*, Croatia Chemica Acta, 74(1), 61-74, 2001; and F. Kozjec et al., *Pharmacokinetics of Ciprofloxacin Metal Complexes*, Acta. Pharm., 46, 109-114, 1996)).

Fluoroquinolones, however, are significantly more soluble in the pharmaceutical compositions of the invention. Accordingly, the invention further relates to a pharmaceutical composition comprising (i) a fluoroquinolone, (ii) a salt formed between a carboxylate anion and a divalent metal cation, and (iii) a liquid comprising (a) an organic solvent selected from the group consisting of glycerol, propylene glycol, glycerol formal, and mixtures thereof and (b) optionally water, wherein the pharmaceutical composition is a solution of the fluoroquinolone in the liquid and the concentration of the fluoroquinolone in the solution is higher than the concentration that can be obtained in the absence of the organic solvent, i.e., wherein the organic solvent is replaced with water.

The pharmaceutical compositions of the invention can be prepared by adding the fluoroquinolone, typically with stirring, to the organic solvent, optionally mixed with water, followed by adding the salt formed between a carboxylate anion and a divalent metal cation, typically with stirring.

In one embodiment, the pharmaceutical compositions of the invention are prepared by adding the salt formed between a carboxylate anion and a divalent metal cation to water followed by adding the fluoroquinolone, typically with stirring. To the resulting mixture is then added the organic solvent to provide the pharmaceutical composition. Preferably, the organic solvent is added soon (i.e., less than 24 h, preferably less than 12 h, more preferably less than 6 h, and most preferably less than 2 h) after the salt formed between a carboxylate anion and a divalent metal cation and the fluoroquinolone are added to the water. The pH of the water preferably ranges from about 5.5 to 8, more preferably about 6 to 7.5, even more preferably about 6 to 7, and most preferably about 6 to 6.5.

Accordingly, the invention further relates to a pharmaceutical composition comprising (i) a fluoroquinolone, (ii) a salt formed between a carboxylate anion and a divalent metal cation, and (iii) a liquid comprising (a) an organic solvent selected from the group consisting of glycerol, propylene glycol, glycerol formal, and mixtures thereof and (b) optionally water, wherein the pharmaceutical composition is prepared by adding the fluoroquinolone and the salt formed between a carboxylate anion and a divalent metal cation to glycerol, propylene glycol, glycerol formal, water, or any combination thereof.

Without wishing to be bound by theory, it is believed that the improved solubility of the fluoroquinolone is due to the formation in the pharmaceutical composition of a complex of formula M$^{+2}$(GLY)(FQ), M$^{+2}$(PG)(FQ), and or M$^{+2}$(GF)(FQ), wherein FQ is the fluoroquinolone or an anion of fluoroquinolone, M$^{+2}$ is a divalent metal cation, GLY is glycerol or an anion of glycerol, PG is propylene glycol or an anion of propylene glycol, and GF is glycerol formal or an anion of glycerol formal. Indeed, analysis of the pharmaceutical compositions of the invention using mass spectral analysis indicates the presence of a complex containing: (i) 1 equivalent of fluoroquinolone; (ii) 1 equivalent of the divalent metal cation, and (iii) 1 equivalent of the organic solvent. Without wishing to be bound by theory, it is believed that the formation of this complex is what leads to the improved solubility of the fluoroquinolone in the liquid.

Accordingly, the invention further relates to a pharmaceutical composition comprising a complex of formula M$^{+2}$(GLY)(FQ), M$^{+2}$(PG)(FQ), and or M$^{+2}$(GF)(FQ), wherein FQ is the fluoroquinolone or an anion of fluoroquinolone, $M^{+2}$ is a divalent metal cation, GLY is glycerol or an anion of glycerol, PG is propylene glycol or an anion of propylene glycol, and GF is glycerol formal or an anion of glycerol formal. As discussed above, the complex can be detected by mass spectral analysis of the pharmaceutical composition. In one embodiment, the pharmaceutical composition is a solution. In one embodiment, the pharmaceutical composition is injectable.

Without wishing to be bound by theory, it is believed that the following reactions take place when a fluoroquinolone and a salt formed between a carboxylate anion and a divalent metal cation are combined in a liquid comprising an organic solvent selected from glycerol, propylene glycol, glycerol formal, and mixtures thereof.

wherein FQ is the fluoroquinolone or an anion of the fluoroquinolone, $M(RCOO^-)_2$ is the salt formed between a carboxylate anion and a divalent metal cation, and OS is the organic solvent, i.e., glycerol, propylene glycol, or glycerol formal. Without wishing to be bound by theory it is believed that the complex M(FQ)(OS) is soluble in the liquid and leads to the increased solubility of the fluoroquinolone.

In contrast, in the absence of the organic solvent, the complex M(FQ)(OS) cannot form. Rather, what is believed to occur is the following reaction to form $M(FQ)_2$:

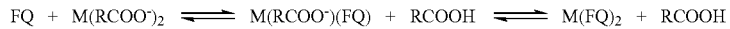

wherein FQ is the fluoroquinolone or an anion of the fluoroquinolone and $M(RCOO^-)_2$ is the salt formed between a carboxylate anion and a divalent metal cation. The complex $M(FQ)_2$, however, is much less soluble than the complex M(FQ)(OS).

In one embodiment, the pharmaceutical composition further comprises a cyclodextrin. The cyclodextrin can be any cyclodextrin known to those skilled in the art. For example, the cyclodextrin can be a α-cyclodextrin, β-cyclodextrin, or γ-cyclodextrin. The cyclodextrin can also be a chemically modified cyclodextrin, for example, a cyclodextrin wherein some or all of the hydroxyl groups of the cyclodextrin are chemically modified to replace some or all of the hydroxyl protons with methyl, hydroxypropyl, carboxymethyl, or acetyl groups (for example, the hydroxypropyl β-cyclodextrin TrappsolHPB®, the randomly methylated β-cyclodextrin TrappsolRMB®, or the 2,6 di-O-methyl β-cyclodextrin TrappsolDMB®, each commercially available from CTD, Inc. of High Springs, Fla.).

Typically, the cyclodextrin is present in an amount ranging from about 0.05 to 5 molar equivalents per equivalent of the fluoroquinolone. In one embodiment, the cyclodextrin is present in an amount ranging from about 0.1 equivalent to 5 equivalents per equivalent of the fluoroquinolone. In one embodiment, the cyclodextrin is present in an amount ranging from about 0.1 equivalent to 2.5 equivalents per equivalent of the fluoroquinolone. In one embodiment, the cyclodextrin is present in an amount ranging from about 0.1 equivalent to 2 equivalents per equivalent of the fluoroquinolone. In one embodiment, the cyclodextrin is present in an amount ranging from about 0.1 equivalent to 1 equivalents per equivalent of the fluoroquinolone.

Without wishing to be bound by theory, it is believed that the presence of the cyclodextrin in the pharmaceutical composition further stabilizes the M(FQ)(OS) complex, possibly by forming an inclusion complex, and/or by shifting the equilibrium to the described M(FQ)(OS) complex. Indeed, when the mass spectrum of a pharmaceutical composition of the invention containing a cyclodextrin is compared to the mass spectrum of a similar pharmaceutical composition, but without the cyclodextrin, the mass spectrum shows a significantly larger amount of the M(FQ)(OS) complex relative to the $M(FQ)_2$ complex in the composition containing the cyclodextrin.

The pharmaceutical compositions of the invention have similar or improved bioavailability compared to commercially available fluoroquinolone compositions, as illustrated in the Examples. The pharmaceutical composition of the invention show similar or improved bioavailability even though salts of fluoroquinolones, particularly salts of fluoroquinolone with a divalent metal cation, are typically significantly less bioavailable compared to fluoroquinolone in the acid form, i.e., fluoroquinolone that is not a salt. (See, for example, S. Lecomte et al., *Effect of Magnesium Complexation by Fluoroquinolones on Their Antibacterial Properties*, Antimicrobial Agents and Chemotherapy, 38:12, 2810-2816, December 1994; Hyoung-Ryun Park, et al., *Ionization and Divalent Cation Complexation of Quinolone Antibiotics in Aqueous Solution*, Bull. Korean Chem. Soc. 2000, 21:9, 849-854; B. Macias, et al., *Complexes of Co(II) and Zn(II) with Ofloxacin, Crystal Structure of $[Co(oflo)_2(MeOH)_2]$$4H_2O$*, J. Pharm. Sci., 91:11, 2416-2423, November 2000; V. Loganathan et al., *In-vitro and In-vivo Drug-Drug Interaction Between Ciprofloxacin and Antacids*, The Eastern Pharmacist, June 1966, 119-121; A. Okhamafe et al., *Pharmacokinetic Interactions of Norfloxacin with Some Metallic Medicinal Agents*, International Journal of Pharmaceutics, 68, (1991), 11-18; B. Lomaestro et al., *Quinolone-Antibiotic Interactions: A Review*, DICP, The Annals of Pharmacotherapy, 25, November 1991, 1249-1258; S. Primozic et al., *Transport Kinetics of Zinc-Ciprofloxacin Complex Across the Model Lipid Membrane*, Farm Vestn, 1999, 50, 294-295; M. Zupancic et al., *Synthesis and Characterization of Two Novel Zinc (II) Complexes With Ciprofloxacin. Crystal Structure of $[C_{17}H_{19}N_3O_3F]_2$$ZnCl_4$$2H_2O$*, Croatia Chemica Acta, 74(1), 61-74, 2001; and F. Kozjec et al., *Pharmacokinetics of Ciprofloxacin Metal Complexes*, Acta. Pharm., 46, 109-114, 1996).

In one embodiment, the divalent metal cation is $Zn^{+2}$, and the carboxylate anion is an optionally substituted $C_1$ to $C_6$ saturated or unsaturated, straight chain or branched alkyl group. In another embodiment, the carboxylate anion is an unsubstituted $C_1$ to $C_6$ saturated or unsaturated, straight chain or branched alkyl group. In another embodiment, the carboxylate anion is an unsubstituted $C_1$ to $C_6$ saturated straight chain or branched alkyl group. In another embodiment, the carboxylate anion is an unsubstituted $C_1$ to $C_6$ saturated straight chain alkyl group. In another embodiment, the carboxylate anion is acetate anion.

In one embodiment, the divalent metal cation is $Mg^{+2}$, and the carboxylate anion acid is an optionally substituted $C_1$ to $C_6$ saturated or unsaturated, straight chain or branched alkyl group. In another embodiment, the carboxylate anion is an unsubstituted $C_1$ to $C_6$ saturated or unsaturated, straight chain or branched alkyl group. In another embodiment, the carboxylate anion is an unsubstituted $C_1$ to $C_6$ saturated straight chain or branched alkyl group. In another embodiment, the carboxylate anion is an unsubstituted $C_1$ to $C_6$ saturated straight chain alkyl group. In another embodiment, the carboxylate anion is acetate anion.

In one embodiment, the divalent metal cation is $Zn^{+2}$, the fluoroquinolone anion is ciprofloxacin anion, and the carboxylate anion is acetate.

In one embodiment, the divalent metal cation is $Zn^{+2}$, the fluoroquinolone anion is enrofloxacin anion, and the carboxylate anion is acetate.

In one embodiment, the divalent metal cation is $Zn^{+2}$, the fluoroquinolone anion is gatifloxacin anion, and the carboxylate anion is acetate.

In one embodiment, the divalent metal cation is $Zn^{+2}$, the fluoroquinolone anion is gemifloxacin anion, and the carboxylate anion is acetate.

In one embodiment, the divalent metal cation is $Zn^{+2}$, the fluoroquinolone anion is levofloxacin anion, and the carboxylate anion is acetate.

In one embodiment, the divalent metal cation is $Zn^{+2}$, the fluoroquinolone anion is lomefloxacin anion, and the carboxylate anion is acetate.

In one embodiment, the divalent metal cation is $Zn^{+2}$, the fluoroquinolone anion is moxifloxacin anion, and the carboxylate anion is acetate.

In one embodiment, the divalent metal cation is $Zn^{+2}$, the fluoroquinolone anion is sparfloxacin anion, and the carboxylate anion is acetate.

In one embodiment, the divalent metal cation is $Zn^{+2}$, the fluoroquinolone anion is trovafloxacin anion, and the carboxylate anion is acetate.

In one embodiment, the divalent metal cation is $Zn^{+2}$, the fluoroquinolone anion is cinofloxacin anion, and the carboxylate anion is acetate.

In one embodiment, the divalent metal cation is $Zn^{+2}$, the fluoroquinolone anion is pefloxacin anion, and the carboxylate anion is acetate.

In one embodiment, the divalent metal cation is $Zn^{+2}$, the fluoroquinolone anion is tosufloxacin anion, and the carboxylate anion is acetate.

In one embodiment, the divalent metal cation is $Zn^{+2}$, the fluoroquinolone anion is temafloxacin anion, and the carboxylate anion is acetate.

In one embodiment, the divalent metal cation is $Zn^{+2}$, the fluoroquinolone anion is fleroxacin anion, and the carboxylate anion is acetate.

In one embodiment, the divalent metal cation is $Zn^{+2}$, the fluoroquinolone anion is amifloxacin anion, and the carboxylate anion is acetate.

In one embodiment, the divalent metal cation is $Zn^{+2}$, the fluoroquinolone anion is binfloxacin anion, and the carboxylate anion is acetate.

In one embodiment, the divalent metal cation is $Zn^{+2}$, the fluoroquinolone anion is danofloxacin anion, and the carboxylate anion is acetate.

In one embodiment, the divalent metal cation is $Zn^{+2}$, the fluoroquinolone anion is marbofloxacin anion, and the carboxylate anion is acetate.

In one embodiment, the divalent metal cation is $Zn^{+2}$, the fluoroquinolone anion is sarafloxacin anion, and the carboxylate anion is acetate.

In one embodiment, the divalent metal cation is $Mg^{+2}$, the fluoroquinolone anion is ciprofloxacin anion, and the carboxylate anion is acetate.

In one embodiment, the divalent metal cation is $Mg^{+2}$, the fluoroquinolone anion is enrofloxacin anion, and the carboxylate anion is acetate.

In one embodiment, the divalent metal cation is $Mg^{+2}$, the fluoroquinolone anion is gatifloxacin anion, and the carboxylate anion is acetate.

In one embodiment, the divalent metal cation is $Mg^{+2}$, the fluoroquinolone anion is gemifloxacin anion, and the carboxylate anion is acetate.

In one embodiment, the divalent metal cation is $Mg^{+2}$, the fluoroquinolone anion is levofloxacin anion, and the carboxylate anion is acetate.

In one embodiment, the divalent metal cation is $Mg^{+2}$, the fluoroquinolone anion is lomefloxacin anion, and the carboxylate anion is acetate.

In one embodiment, the divalent metal cation is $Mg^{+2}$, the fluoroquinolone anion is moxifloxacin anion, and the carboxylate anion is acetate.

In one embodiment, the divalent metal cation is $Mg^{+2}$, the fluoroquinolone anion is sparfloxacin anion, and the carboxylate anion is acetate.

In one embodiment, the divalent metal cation is $Mg^{+2}$, the fluoroquinolone anion is trovafloxacin anion, and the carboxylate anion is acetate.

In one embodiment, the divalent metal cation is $Mg^{+2}$, the fluoroquinolone anion is cinofloxacin anion, and the carboxylate anion is acetate.

In one embodiment, the divalent metal cation is $Mg^{+2}$, the fluoroquinolone anion is pefloxacin anion, and the carboxylate anion is acetate.

In one embodiment, the divalent metal cation is $Mg^{+2}$, the fluoroquinolone anion is tosufloxacin anion, and the carboxylate anion is acetate.

In one embodiment, the divalent metal cation is $Mg^{+2}$, the fluoroquinolone anion is temafloxacin anion, and the carboxylate anion is acetate.

In one embodiment, the divalent metal cation is $Mg^{+2}$, the fluoroquinolone anion is fleroxacin anion, and the carboxylate anion is acetate.

In one embodiment, the divalent metal cation is $Mg^{+2}$, the fluoroquinolone anion is amifloxacin anion, and the carboxylate anion is acetate.

In one embodiment, the divalent metal cation is $Mg^{+2}$, the fluoroquinolone anion is binfloxacin anion, and the carboxylate anion is acetate.

In one embodiment, the divalent metal cation is $Mg^{+2}$, the fluoroquinolone anion is danofloxacin anion, and the carboxylate anion is acetate.

In one embodiment, the divalent metal cation is $Mg^{+2}$, the fluoroquinolone anion is marbofloxacin anion, and the carboxylate anion is acetate.

In one embodiment, the divalent metal cation is $Mg^{+2}$, the fluoroquinolone anion is sarafloxacin anion, and the carboxylate anion is acetate.

In one embodiment, the pharmaceutical composition comprises a fluoroquinolone; zinc acetate; and a liquid comprising about 75 percent glycerol, propylene glycol, glycerol formal, or a mixture thereof by volume of the liquid and about 25 percent water by volume of the liquid, and the ratio of fluoroquinolone to zinc acetate is about 2 to 1.

In one embodiment, the pharmaceutical composition comprises a fluoroquinolone; zinc acetate; and a liquid comprising about 80 percent glycerol, propylene glycol, glycerol formal, or a mixture thereof by volume of the liquid and about 20 percent water by volume of the liquid, and the ratio of fluoroquinolone to zinc acetate is about 2 to 1.

In one embodiment, the pharmaceutical composition comprises a fluoroquinolone; magnesium acetate; and a liquid comprising about 75 percent glycerol, propylene glycol, glycerol formal, or a mixture thereof by volume of the liquid and about 25 percent water by volume of the liquid, and the ratio of fluoroquinolone to magnesium acetate is about 2 to 1.

In one embodiment, the pharmaceutical composition comprises a fluoroquinolone; magnesium acetate; and a liquid comprising about 80 percent glycerol, propylene glycol, glycerol formal, or a mixture thereof by volume of the liquid and about percent volume by weight of the liquid, and the ratio of fluoroquinolone to magnesium acetate is about 2 to 1.

In one embodiment, the pharmaceutical composition comprises a fluoroquinolone; zinc acetate; and a liquid comprising about 75 percent glycerol, propylene glycol, glycerol formal, or a mixture thereof by volume of the liquid and about percent water by volume of the liquid, and the ratio of fluoroquinolone to zinc acetate is about 1 to 1.

In one embodiment, the pharmaceutical composition comprises a fluoroquinolone; zinc acetate; and a liquid comprising about 80 percent glycerol, propylene glycol, glycerol formal, or a mixture thereof by volume of the liquid and about percent water by volume of the liquid, and the ratio of fluoroquinolone to zinc acetate is about 1 to 1.

In one embodiment, the pharmaceutical composition comprises a fluoroquinolone; magnesium acetate; and a liquid comprising about 75 percent glycerol, propylene glycol, glycerol formal, or a mixture thereof by volume of the liquid and about percent water by volume of the liquid, and the ratio of fluoroquinolone to magnesium acetate is about 1 to 1.

In one embodiment, the pharmaceutical composition comprises a fluoroquinolone, zinc acetate, and a liquid comprising about 75 percent glycerol by volume of the liquid and about 25 percent water by volume of the liquid, and the ratio of fluoroquinolone to zinc acetate is about 2 to 1.

In one embodiment, the pharmaceutical composition comprises a fluoroquinolone, zinc acetate, and a liquid comprising about 80 percent glycerol by volume of the liquid and about 20 percent water by volume of the liquid, and the ratio of fluoroquinolone to zinc acetate is about 2 to 1.

In one embodiment, the pharmaceutical composition comprises a fluoroquinolone, magnesium acetate, and a liquid comprising about 75 percent glycerol by volume of the liquid and about 25 percent water by volume of the liquid, and the ratio of fluoroquinolone to magnesium acetate is about 2 to 1.

In one embodiment, the pharmaceutical composition comprises a fluoroquinolone, magnesium acetate, and a liquid comprising about 80 percent glycerol by volume of the liquid and about 20 percent volume by weight of the liquid, and the ratio of fluoroquinolone to magnesium acetate is about 2 to 1.

In one embodiment, the pharmaceutical composition comprises a fluoroquinolone, zinc acetate, and a liquid comprising about 75 percent glycerol by volume of the liquid and about 25 percent water by volume of the liquid, and the ratio of fluoroquinolone to zinc acetate is about 1 to 1.

In one embodiment, the pharmaceutical composition comprises a fluoroquinolone, zinc acetate, and a liquid comprising about 80 percent glycerol by volume of the liquid and about 20 percent water by volume of the liquid, and the ratio of fluoroquinolone to zinc acetate is about 1 to 1.

In one embodiment, the pharmaceutical composition comprises a fluoroquinolone, magnesium acetate, and a liquid comprising about 75 percent glycerol by volume of the liquid and about 25 percent water by volume of the liquid, and the ratio of fluoroquinolone to magnesium acetate is about 1 to 1.

In one embodiment, the pharmaceutical composition comprises a fluoroquinolone, magnesium acetate, and a liquid comprising about 80 percent glycerol by volume of the liquid and about 20 percent volume by weight of the liquid, and the ratio of fluoroquinolone to magnesium acetate is about 1 to 1.

Methods of Treatment

Due to their activity, the pharmaceutical compositions comprising (i) a fluoroquinolone, (ii) a salt formed between a carboxylate anion and a divalent metal cation, and (iii) a liquid comprising (a) an organic solvent selected from the group consisting of glycerol, propylene glycol, glycerol formal, and mixtures thereof and (b) optionally water are advantageously useful in veterinary and human medicine. The pharmaceutical compositions are particularly useful for treating or preventing a bacterial infection or a nephrotic syndrome in an animal in need thereof.

Accordingly, the invention further relates to methods of treating or preventing a condition in an animal comprising administering to an animal in need thereof an effective amount of a pharmaceutical composition of the invention.

In one embodiment, the invention relates to methods of treating a condition in an animal comprising administering to an animal in need thereof an effective amount of a pharmaceutical composition of the invention.

In one embodiment, the invention relates to methods of preventing a condition in an animal comprising administering to an animal in need thereof an effective amount of a pharmaceutical composition of the invention.

In one embodiment, the animal is a mammal.
In one embodiment, the animal is a canine, a feline, an equine, a bovine, an ovine, or a porcine.
In one embodiment the animal is a human.
In one embodiment, the animal is a non-human animal.
In one embodiment, the animal is a dog.
In one embodiment, the animal is a cat.
In one embodiment, the animal is a cow.
In one embodiment, the animal is a pig.
In one embodiment, the animal is a horse.
In one embodiment, the animal is a sheep.
In one embodiment, the animal is a monkey.
In one embodiment, the animal is a baboon.
In one embodiment, the animal is a rat.
In one embodiment, the animal is a mouse.
In one embodiment, the animal is a guinea pig.
In one embodiment, the condition is a bacterial infection.
In one embodiment, the condition is a bacterial infection caused by *Staphylococcus aureus, Streptococcus pneumoniae*, coagulese-negative staphylococci, *Streptococcus pyogenes, Staphylococcus epidermis, Pseudomonas aeruginosa, Escherichia coli, Klebsiella pneumoniae, Enterobacter cloacae, Proteus mirabilis, Proteus vulgaris, Providencia stuartii, Morganella morganii, Citrobacter diversus, Citrobacter freundii, Haemophilus influenzae*, or *Neisseria gonorrhea*.

In one embodiment, the condition is a respiratory tract infection, a urinary tract infection, a postoperative-wound infection, a bone or joint infection, a skin infection, an ear infection, or a sexually transmitted disease.

In one embodiment, the condition is a nephrotic syndrome.

The effective amount administered to the animal depends on a variety of factors including, but not limited to the type of animal being treated, the condition being treated, the severity of the condition, the specific fluoroquinolone being administered and the susceptibility of the infecting organism to the fluoroquinolone being administered. The amount of the pharmaceutical composition that is effective in the treatment or prevention of a condition, such as a bacterial infection, can be determined by standard clinical techniques. In addition, in vitro or in vivo assays can optionally be employed to help identify optimal dosage ranges. One of ordinary skill in the art will readily be able determine the precise dose to be employed. Suitable effective dosage amounts, however, typically range from about 0.1 mg/kg of body weight to about 50 mg/kg of body weight, preferably about 0.5 mg/kg of body weight to about 25 mg/kg of body weight, more preferably 0.75 mg/kg of body weight to about 20 mg/kg of body weight, and most preferably 1 mg/kg of body weight to about 15 mg/kg of body weight. The effective dosage amounts described herein refer to total amounts administered, that is, if more than one fluoroquinolone is administered, the effective dosage amounts correspond to the total amount administered.

For example when the fluoroquinolone is ciprofloxacin the divalent metal cation is $Zn^{+2}$, and the carboxylate anion is acetate, the condition is a bacterial infection, and the animal is a dog, an effective amount is typically between about 2.5 and 10 mg of ciprofloxacin/lb (between about 5 and 30 mg of ciprofloxacin/kg) administered orally once a day or two times per day until 2-3 days after cessation of the condition. When the fluoroquinolone is ciprofloxacin the divalent metal cation is $Zn^{+2}$, and the carboxylate anion is acetate, the condition is a bacterial infection, and the animal is a cat, an effective amount is typically not more than 5 mg of fluoroquinolone/kg administered orally once a day until 2-3 days after cessation of the condition.

In one embodiment, the pharmaceutical compositions are administered parenterally.

In one embodiment, the pharmaceutical compositions are administered subcutaneously.

In one embodiment, the pharmaceutical compositions are administered intravenously.

In one embodiment, the pharmaceutical compositions are administered orally.

In one embodiment, the effective amount of the pharmaceutical composition is administered once per day until 2-3 days after cessation of the condition.

In one embodiment, the effective amount of the pharmaceutical composition is administered as two doses per day until 2-3 days after cessation of the condition.

In one embodiment, effective amount of the pharmaceutical composition is administered once per day for 7 days.

In one embodiment, the effective amount of the pharmaceutical composition is administered as two doses per day for 7 days.

In one embodiment, the effective amount of the pharmaceutical composition is administered once per day for 14 days.

In one embodiment, the effective amount of the pharmaceutical composition is administered as two doses per day for 14 days.

In one embodiment, the effective amount of the pharmaceutical composition is administered once per day for 21 days.

In one embodiment, the effective amount of the pharmaceutical composition is administered as two doses per day for 21 days.

To treat some conditions, the pharmaceutical compositions of the invention can be administered for even longer periods of time, for example several months.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Example 1

Oral Liquid Enrofloxacin Composition—Zinc Cation and Strawberry Flavored 2.3 gr of enrofloxacin and 0.7024 gr of zinc acetate were mixed well with 15 mL of de-ionized water in a 100 ml volumetric flask. To the resulting composition was added 60 mL of glycerol with mixing to provide a homogeneous solution. To this solution was added 5 mL of strawberry flavor and the resulting solution mixed well. The volume of the solution was made up to 100 mL with glycerol and mixed well to provide a liquid oral enrofloxacin formulation. The concentration of enrofloxacin in the formulation is 23 mg/mL.

A pharmaceutical composition similar to that described above can be prepared except that the flavoring is not included in the composition and the pharmaceutical composition is sterile filtered to provide an injectable pharmaceutical composition.

Example 2

Oral Liquid Enrofloxacin Composition—Magnesium Cation and Strawberry Flavored 575 mg of enrofloxacin and 114 mg of magnesium acetate (0.8 mL of 1 M aqueous solution, commercially available from Sigma-Aldrich of Milwaukee, Wis.) were mixed well with 3.75 mL of de-ionized water in a 25 mL volumetric flask. To the resulting composition was added 15 mL of glycerol with mixing to provide a homogeneous solution. To the resulting solution was added 1.25 mL of strawberry flavor with mixing. The volume of the solution was made up to 25 mL with glycerol and mixed well to provide a liquid oral enrofloxacin formulation. The concentration of enrofloxacin in the formulation is 23 mg/mL.

A pharmaceutical composition similar to that described above can be prepared except that the flavoring is not included in the composition and the pharmaceutical composition is sterile filtered to provide an injectable pharmaceutical composition.

Example 3

Oral Liquid Enrofloxacin Composition—Magnesium Cation and Mint Flavored 575 mg of enrofloxacin and 114 mg of magnesium acetate (0.8 mL of 1 M aqueous solution, commercially available from Sigma-Aldrich of Milwaukee, Wis.) were mixed well with 3.75 mL of de-ionized water in a 25 ml volumetric flask. To the resulting composition was added 15 mL of glycerol with mixing to provide a homogeneous solution. To the resulting solution was added 1.25 mL of mint oil with mixing. The volume of the solution was made up to 25 mL with glycerol and mixed well to provide a liquid oral enrofloxacin formulation. The concentration of enrofloxacin in the formulation is 23 mg/mL.

A pharmaceutical composition similar to that described above can be prepared except that the flavoring is not included in the composition and the pharmaceutical composition is sterile filtered to provide an injectable pharmaceutical composition.

Example 4

Administration of Oral Liquid Enrofloxacin to Dogs

Three tablets (22.7 mg per tablet, total 68 mg) of commercially available enrofloxacin (Baytril®, commercially available from Bayer Health Care of Shawnee Mission, Kans.) was orally administered to each of two dogs. To each of another two dogs was orally administered 3 mL of the liquid enrofloxacin composition of Example 2. For each dog, the concentration of enrofloxacin in serum was determined as a function of time over a period of about 24 hours. Blood samples were obtained as a function of time and frozen.

For analysis of the blood samples the following procedure was followed:
 1) Thaw sample completely and mix well;
 2) Transfer 200 μl of the sample into a microfuge tube;
 3) Add 400 μl of methanol and mix well;
 4) Centrifuge at 13,000 rpm, −9° C. for 15 minutes;
 5) Transfer the supernatant to a 20 mL scintillation vial and add 3,400 μl of mobile phase A (described below);
 6) Mix well, filter using a Acrodisc 13 mm syringe filter with 0.2 μm membrane and analyze by HPLC using the following conditions:

| | |
|---|---|
| Column: | Waters X Bridge C-18 4.6 mm × 50 mm column equipped with a Gemini 4 mm × 3 mm guard cartridge. |
| Injection Volume: | 20 μL |
| Flow Rate: | 2 mL/min., isochratic 85% mobile phase A 15% mobile phase B |
| Mobile Phase: Composition: | |
| A: | 100 mM phosphate buffer - pH 2.1 |
| B: | Methanol |
| Acquisition Wavelength: | 274 nm |
| Fluorescence: | Excitation: 297 nm Emission: 440 nm Gain 1000 Attenuation: 4 |
| Run time: | 10 min. |

At the end of each analysis, the column is washed with 90 percent aqueous methanol.

Mobile phase A can be prepared by the following procedure:
 1. Weigh 13.8 g of sodium phosphate monobasic monohydrate into a 1 liter beaker.
 2. Add 500 mL of de-ionized water with stirring.
 3. Adjust the pH to 2.11 with phosphoric acid.
 4. Transfer the resulting solution into a 1 liter volumetric flask and fill with water to the mark and mix well.

The concentration of enrofloxacin was determined by comparing the enrofloxacin peak area obtained from HPLC analysis of the sample to a standard curve of peak area versus concentration of enrofloxacin obtained by HPLC analysis of several samples of known enrofloxacin concentration.

The standard curve was obtained by weighing 100 mg of commercially available enrofloxacin into a 100 mL volumetric flask and filling the flask to 100 mL with methanol to provide a 1 mg/mL enrofloxacin stock solution. The 1 mg/mL enrofloxacin stock solution was then diluted with methanol to provide various standards by adding 5 mL of the 1 mg/mL enrofloxacin stock solution to 500 mL of methanol to provide a 10 μg/mL standard, adding 0.25 mL of the 1 mg/mL enrofloxacin stock solution to 100 mL of methanol to provide a 0.025 μg/mL standard, adding 0.5 mL of the 1 mg/mL enrofloxacin stock solution to 100 mL of methanol to provide a 0.05 μg/mL standard, adding 1 mL of the 1 mg/mL enrofloxacin stock solution to 100 mL of methanol to provide a 0.1 μg/mL standard, adding 3 mL of the 1 mg/mL enrofloxacin stock solution to 100 mL of methanol to provide a 0.3 μg/mL standard, adding 7 mL of the 1 mg/mL enrofloxacin stock solution to 100 mL of methanol to provide a 0.70 μg/mL standard, adding 15 mL of the 1 mg/mL enrofloxacin stock solution to 100 mL of methanol to provide a 1.5 μg/mL standard.

200 μL of blank serum was then placed in each of four microfuge tubes labeled standard for points 1, 2, 3, and 4. To the tubes labeled standard for points 1, 2, 3, and 4 was then added 200 μL of the 0.025 μg/mL standard, 0.05 μg/mL standard, 0.1 μg/mL standard, 0.3 μg/mL standard, respectively. 200 μL of methanol was then added to each of the tubes; the resulting mixtures mixed with a vortex mixture for about 20 seconds; and then centrifuged at 13,000 rpm at −9° C. for 15 minutes. The resulting supernatant of each sample was then transferred to individual 20 mL scintillation vial and 1400 mL of mobile phase A was added to each supernatant. Each resulting solution was then mixed well, filtered using a Acrodisc 13 mm syringe filter with 0.2 μm membrane and analyze by HPLC using the HPLC method described above to provide the standard curve.

FIG. 1 is a graphical representation of the concentration of enrofloxacin in serum in μg/mL as a function of time for each dog. The symbol (■) represents data points for administration of the solid dosage form of commercially available enrofloxacin (i.e., Baytril®) and the symbol (♦) represents data points for administration of enrofloxacin as the liquid pharmaceutical formulation of the invention. The data demonstrates that the oral liquid formulation is bioavailable. FIG. 1 shows that each dosage form has a similar $C_{max}$ but that the pharmaceutical composition of the invention was 10 percent more bioavailable, as measured by area under the curve.

Example 5

Administration of Oral Liquid Enrofloxacin to Cats

A single tablet (22.7 mg) of commercially available enrofloxacin (Baytril®, commercially available from Bayer Health Care of Shawnee Mission, Kans.) was orally administered to each of two cats. 1 mL of the liquid enrofloxacin composition of Example 1 was orally administered to each of two cats. For each cat, the concentration of enrofloxacin in serum was determined as a function of time over a period of about 24 hours using the method described above in Example 4.

Figure 2:
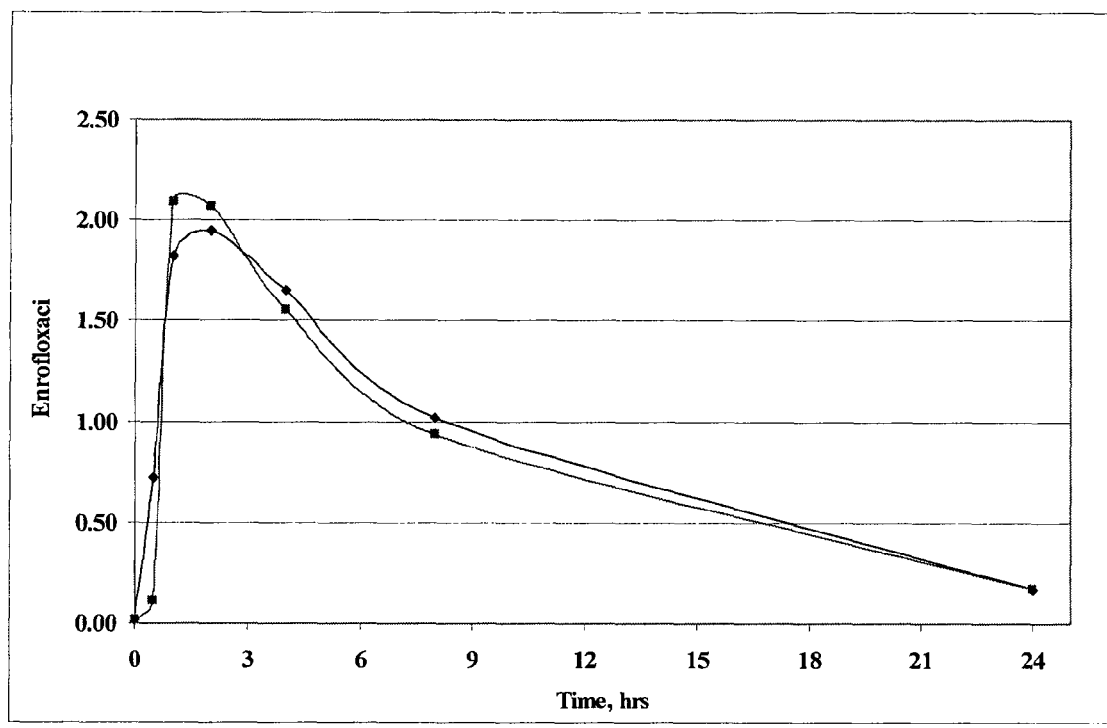
FIG. 2 is a graphical representation of the concentration of enrofloxacin in serum in µg/mL as a function of time (hours) when enrofloxacin is orally administered to a cat. The symbol (■) represents data points for administration of a single tablet (22.7 mg) of commercially available enrofloxacin (i.e., Baytril) at a dose of 22.7 mg/mL and the symbol (♦) represents data points for administration of enrofloxacin as liquid pharmaceutical formulation of the invention at a dose of 23 mg (i.e., 1 mL of a liquid composition of the invention having an enrofloxacin concentration of 23 mg/mL).

FIG. 2 is a graphical representation of the concentration of enrofloxacin in serum as a function of time. Each data point represents the serum concentration of enrofloxacin in μg/mL. (Each data point represents the average of the serum concentration for two cats. The symbol (■) represents data points for administration of the solid dosage form of commercially available enrofloxacin (i.e., Baytril®) and the symbol (▲) represents data points for administration of enrofloxacin as liquid pharmaceutical formulation of Example 1. The data demonstrates that the oral liquid formulation is bioavailable.

Example 6

Administration of Oral Liquid Enrofloxacin to Cats

A single tablet (22.7 mg) of commercially available enrofloxacin (Baytril, commercially available from Bayer Health Care of Shawnee Mission, Kans.) was orally administered to each of three cats. To each of three cats was orally administered 1 mL of the liquid enrofloxacin composition of Example 1. To each of three cats was orally administered 1 mL of the liquid enrofloxacin composition of Example 2 and to another three cats was orally administered 1 mL of the liquid enrofloxacin composition of Example 3. For each group of cats, the concentration of enrofloxacin in serum was determined as a function of time over a period of about 24 hours using the method described above in Example 4.

Figure 3:
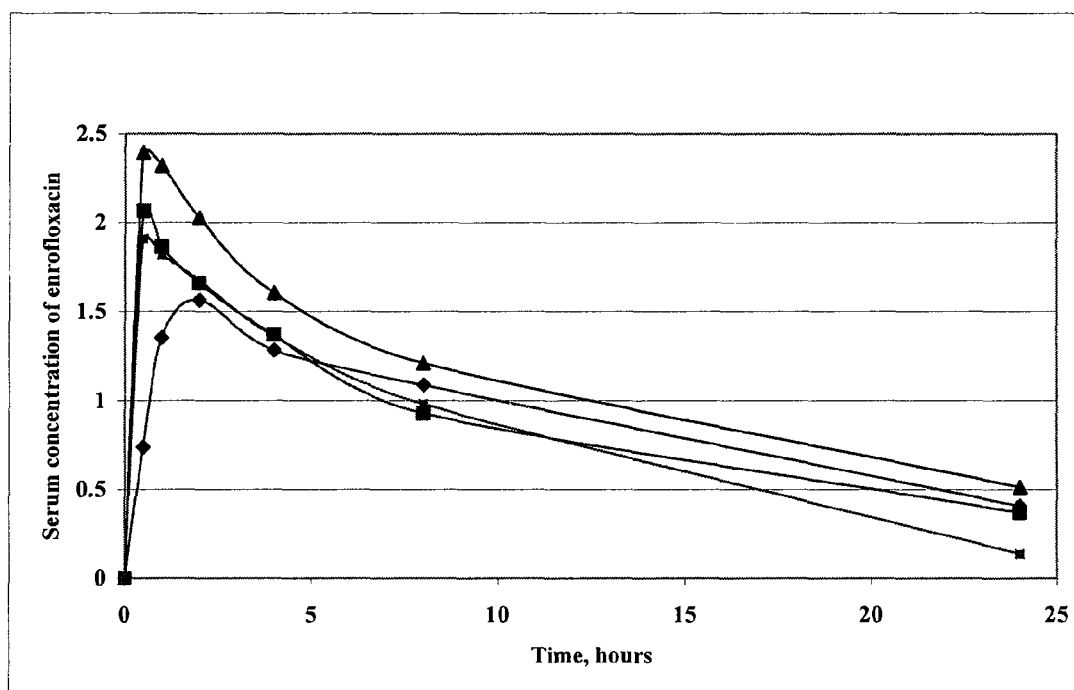
FIG. 3 is a graphical representation of the concentration of enrofloxacin in serum in µg/mL as a function of time (hours) when enrofloxacin is orally administered to a cat. The symbol (♦) represents data points for administration of a single tablet (22.7 mg) of commercially available enrofloxacin (i.e., Baytril) and the symbols (■), (▲), (■) and represents data points for administration of enrofloxacin as a liquid pharmaceutical formulation of the invention at a dose of 23 mg (i.e., 1 mL of a liquid composition of the invention having an enrofloxacin concentration of 23 mg/mL).

FIG. 3 is a graphical representation of the concentration of enrofloxacin in serum as a function of time. Each data point represents the serum concentration of enrofloxacin in μg/mL. Each data point represents the average of the serum concentration for the three cats. The symbol (♦) represents data points for administration of the solid dosage form of commercially available enrofloxacin (i.e., Baytril). The symbol (■) represents data points for administration of enrofloxacin as liquid pharmaceutical formulation of Example 1. The symbol (▲) represents data points for administration of enrofloxacin as liquid pharmaceutical formulation of Example 2. The symbol (■) represents data points for administration of enrofloxacin as liquid pharmaceutical formulation of Example 3. The data demonstrates that the oral liquid formulation is bioavailable.

Example 7

Mass Spectral Analysis of the Pharmaceutical Composition

A: A pharmaceutical composition was prepared by suspending 1.15 g of enrofloxacin and 702.4 mg of zinc acetate in 10 mL of water and mixing the suspension well. The resulting mixture was then filled to a volume of 50 mL with glycerol and mixed to provide a homogeneous solution. The pharmaceutical composition can be sterile filtered to provide an injectable formulation.

B: A second pharmaceutical composition was prepare by suspending 575 mg of enrofloxacin and 354.7 mg of zinc acetate in 5 mL of water and mixing the suspension well. To the resulting composition was added 238 mg of β-cyclodextrin (commercially available from Sigma-Aldrich of Milwaukee, Wis.) and the resulting mixture mixed well with a vortex mixer. The flask was then filled to a volume of 25 mL with glycerol and mixed to provide a homogeneous solution. The pharmaceutical composition can be sterile filtered to provide an injectable formulation.

Pharmaceutical compositions A and B are identical except that pharmaceutical composition B also includes β-cyclodextrin.

Each of the above solutions was analyzed by mass spectroscopy using an Applied Biosystem QTRAP LC/MS/MS system, serial number m2170311. The following procedure was followed to obtain the mass spectrum:

1 drop of the pharmaceutical composition is added to a clean scintillation vial;

20 mL of methanol is added to the scintillation vial and the contents of the vial are mixed using a vortex mixer;

a portion of the contents of the vial are drawn into a 1 mL Hamilton gas tight syringe and the contents of syringe are infused into the mass spectrometer using a Harvard syringe pump at a flow rate of 10 μL/min.; and the mass spectrum is obtained.

The mass spectral data was analyzed using Analyst version 1.4 software and the mass spectrometer was operated using the following parameters:

Ion source: Turbo spray
Curtain gas (CUR): 40
Ion spray voltage (IS): 5500
Temperature (TEM): 0.0
Ion source gas 1 (GS1): 20
Ion source gas 2 (GS2) 0
Declustering potential (DP): 45
Entrance potential (EP): 10
Quad 1 Ion energy 1 (IE1): 0.8
Q1 resolution is sent to unit
Deflector (DF): −150.0
CEM: 2800

Figure 4:
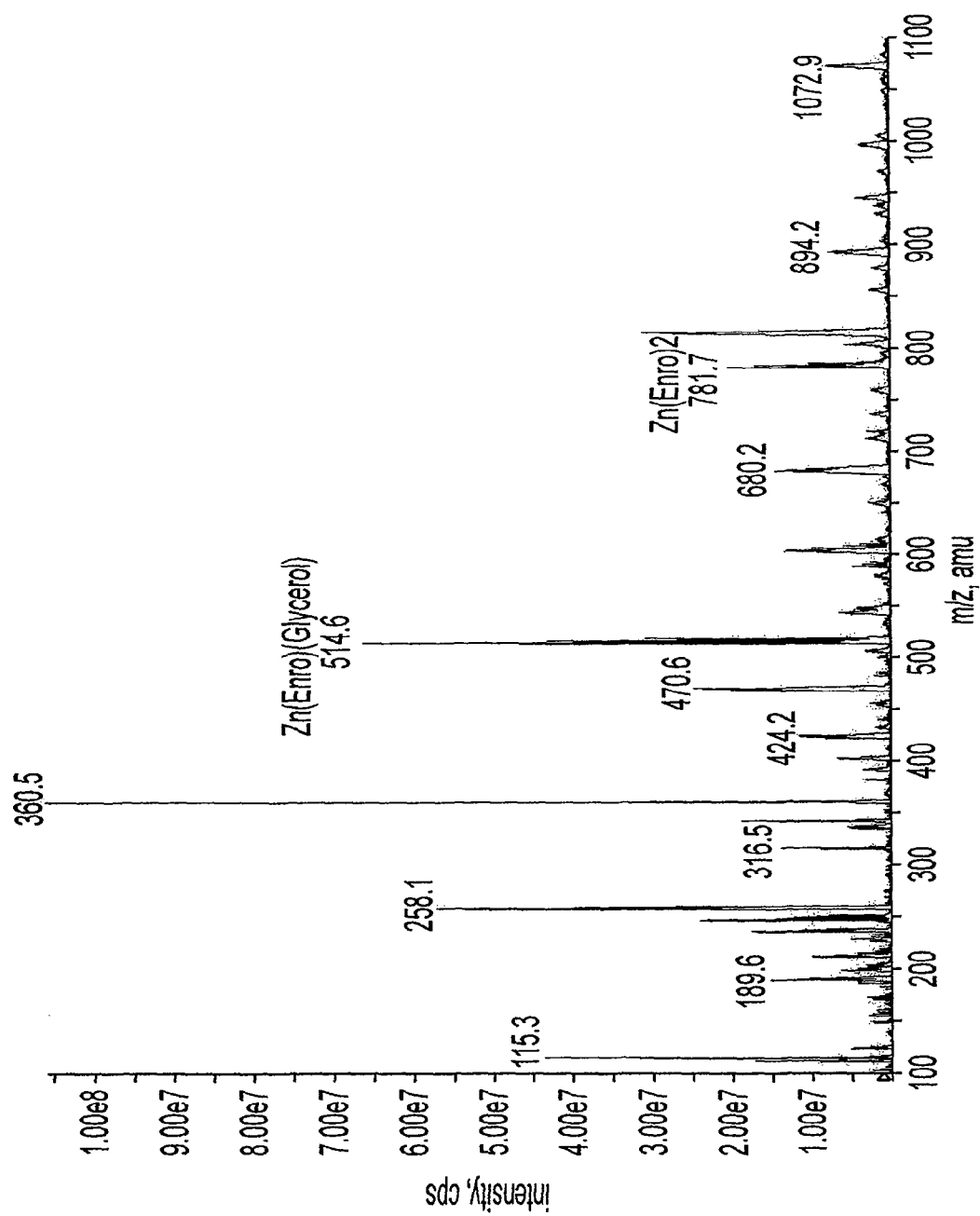
FIG. 4 is the mass spectrum of the pharmaceutical composition prepared in Example 7A.
Figure 5:
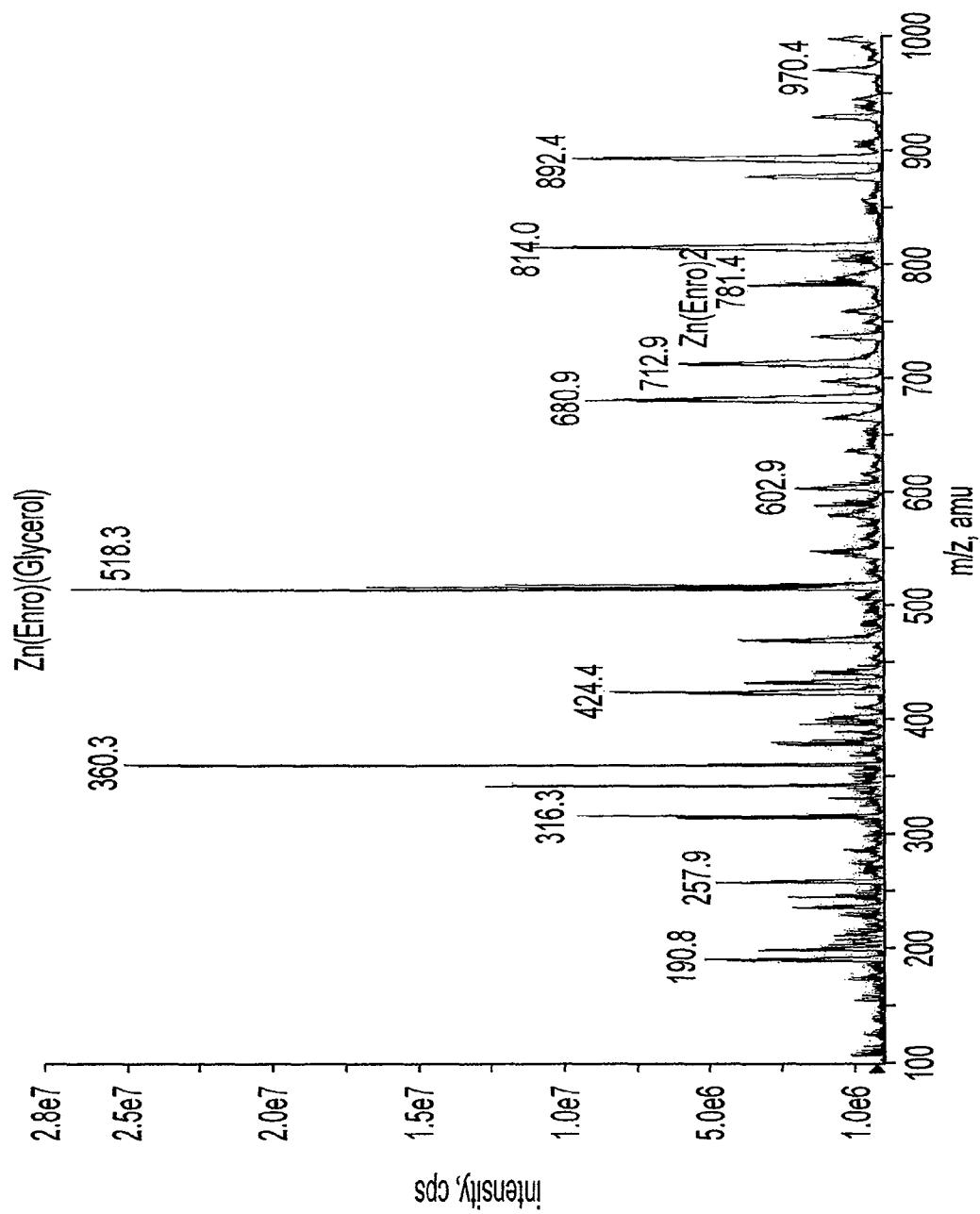
FIG. 5 is the mass spectrum of the pharmaceutical composition prepared in Example 7B.

The mass spectrum of pharmaceutical composition A and B are shown in FIG. 4 and FIG. 5, respectively. A comparison of the mass spectrum of pharmaceutical composition A (FIG. 4) and pharmaceutical composition B (FIG. 5) shows that the ratio of the Zn(enrofloxacin)(glycerol) complex to the Zn(enrofloxacin)$_2$ complex is significantly larger in pharmaceutical composition B, which contains β-cyclodextrin.

Example 8

Mass Spectral Analysis of the Pharmaceutical Composition

A pharmaceutical composition was prepared by combining 575 mg of enrofloxacin and 230 mg of magnesium acetate (1.62 mL of a 1M solution in water, commercially available from Sigma-Aldrich of Milwaukee, Wis.) in 8.38 ml of water to provide a suspension and mixing the suspension well to provide a clear solution. To the resulting solution was added 238 mg of β-cyclodextrin (commercially available from Sigma-Aldrich of Milwaukee, Wis.) and the resulting mixture mixed well with a vortex mixer to provide a clear solution. The clear solution was filled to a volume of 25 mL with glycerol to provide a homogeneous solution. The pharmaceutical composition can be sterile filtered to provide an injectable formulation.

Figure 6:
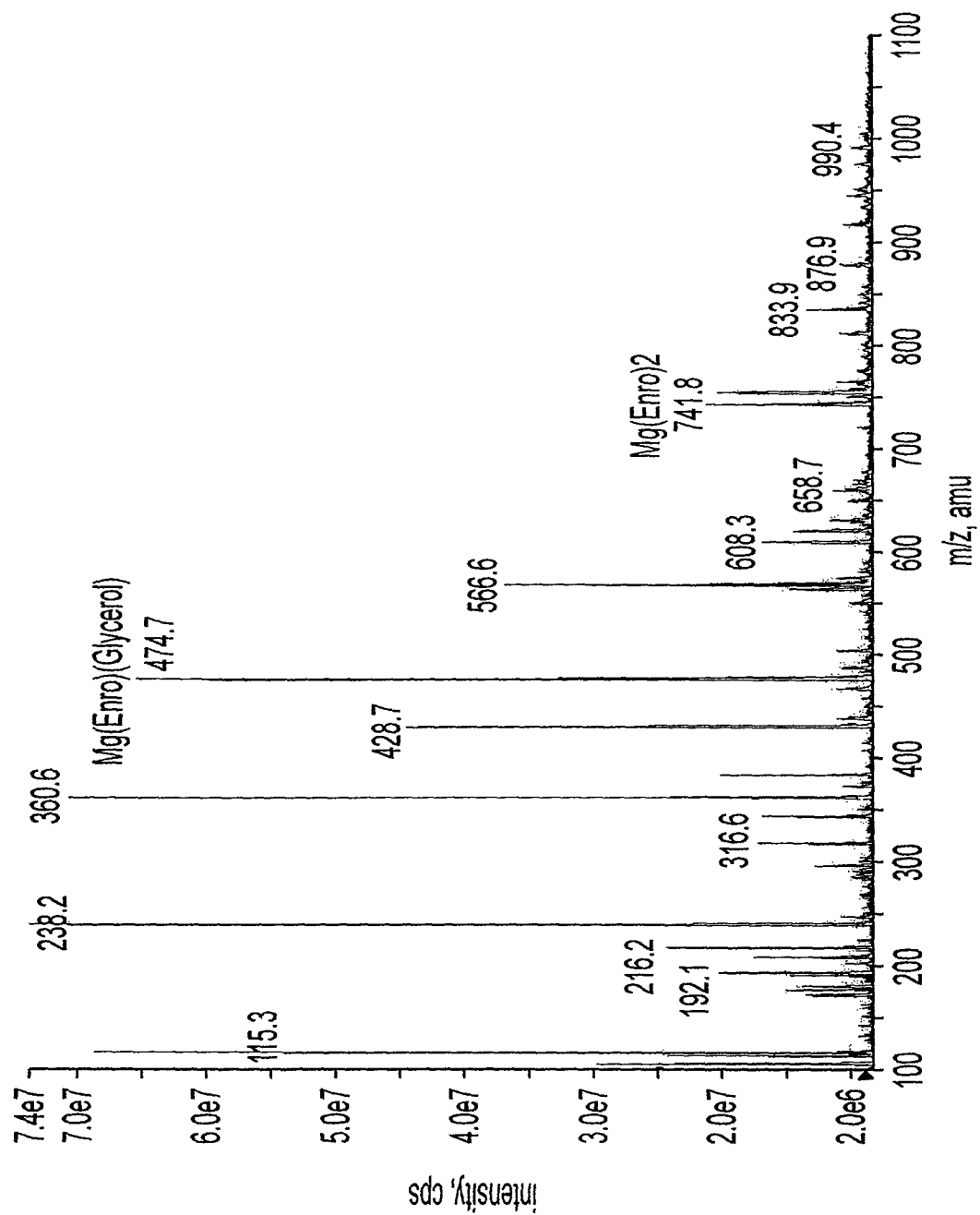
FIG. 6 is the mass spectrum of the pharmaceutical composition prepared in Example 8.

The pharmaceutical composition was analyzed by mass spectroscopy using the analysis conditions described in Example 7. The mass spectrum is provided in FIG. 6. The mass spectrum shows the presence of the Mg(enrofloxacin)(glycerol) complex.

Example 9

Liquid Pharmaceutical Composition with Enrofloxacin and Zinc Acetate

A pharmaceutical composition was prepared by suspending 575 mg of enrofloxacin and 354.7 mg of zinc acetate in 5 mL of de-ionized water in a 25 mL volumetric flask and the resulting suspension mixed well. 10 mL of propylene glycol was then added to the resulting suspension with mixing to provide a homogeneous clear solution. To the resulting solution was then added 1.818 g of β-cyclodextrin (commercially available from Sigma-Aldrich of Milwaukee, Wis.) and the volume of the solution made up to 25 mL with glycerol. The resulting composition was then mixed and intermittently placed in a sonic bath until the cyclodextrin dissolved to provide a clear solution. The concentration of enrofloxacin in the resulting pharmaceutical composition is 23 mg/mL.

Example 10

Liquid Pharmaceutical Composition with Ciprofloxacin and Zinc Acetate

A pharmaceutical composition was prepared by suspending 526 mg of ciprofloxacin and 3.551 mg of zinc acetate in 10 mL of de-ionized water in a 50 mL volumetric flask. The resulting suspension was mixed well, the volume of the flask filled to 50 mL with glycerol, and the resulting composition mixed well to provide a clear solution. The resulting pharmaceutical composition has a ciprofloxacin concentration of 10.5 mg/mL (10.5 percent by weight).

Example 11

Liquid Pharmaceutical Composition with Ofloxacin and Zinc Acetate

A pharmaceutical composition was prepared by suspending 1.156 g of ofloxacin and 710.2 mg of zinc acetate in 10 mL of de-ionized water in a 50 mL volumetric flask. The resulting suspension was mixed well, the volume of the flask filled to 50 mL with glycerol, and the resulting composition mixed well to provide a clear solution. The resulting pharmaceutical composition has an ofloxacin concentration of greater than 2 percent by weight. In contrast, it was not possible to obtain a solution having an ofloxacin concentration of even 1 percent by weight when ofloxacin was added to water, ethanol, methanol, glycerol formal, propylene glycol, or N-methylpyrrolidone.

Example 12

Liquid Pharmaceutical Composition with Ofloxacin and Magnesium Acetate and Cyclodextrin A pharmaceutical composition was prepared by combining 1.156 g of ofloxacin, 1.765 mL of de-ionized water, 3.235 mL of 1M aqueous magnesium acetate solution (commercially available from Sigma-Aldrich of Milwaukee, Wis.) in a 50 mL volumetric flask and adding 20 mL of propylene glycol to the resulting mixture. The resulting mixture was then mixed well using a vortex mixer, 3.6 g of β-cyclodextrin (commercially available from Sigma-Aldrich of Milwaukee, Wis.) added, and the resulting mixture mixed well using a vortex mixer. The volumetric flask was then filled to a volume of about 40 mL with glycerol and sonicated to provide a clear solution. The volume of the volumetric flask was then filled to a volume of 50 mL and the resulting solution mixed well to provide the pharmaceutical composition. The concentration of ofloxacin in the pharmaceutical composition is 23 mg/mL.

Example 13

Liquid Pharmaceutical Composition with Enrofloxacin and Magnesium Acetate 2.3 gr of enrofloxacin, 6.47 mL of 1M aqueous magnesium acetate solution (commercially available from Sigma-Aldrich of Milwaukee, Wis.), and 8.53 mL of de-ionized water were combined in a 100 mL volumetric flask and the resulting composition mixed well using a vortex mixer. The volumetric flask was then filled to a volume of about 75 mL with glycerol and the resulting mixture sonicated to provide a clear solution. To the resulting solution was added 5 mL of aqueous strawberry flavor, the solution mixed well, the volumetric flask filled to a volume of 100 mL with glycerol, and the resulting solution mixed well to provide the pharmaceutical composition. The concentration of enrofloxacin in the pharmaceutical composition is 23 mg/mL.

Example 14

Administration of Oral Liquid Enrofloxacin to Cats

A single tablet (22.7 mg) of commercially available enrofloxacin (Baytril®, commercially available from Bayer Health Care of Shawnee Mission, Kans.) was orally administered to each of three cats. 1 mL of the liquid enrofloxacin composition of Example 13 was orally administered to each of three cats. For each cat, the concentration of enrofloxacin in serum was determined as a function of time over a period of about 24 hours using the method described above in Example 4.

Figure 7:
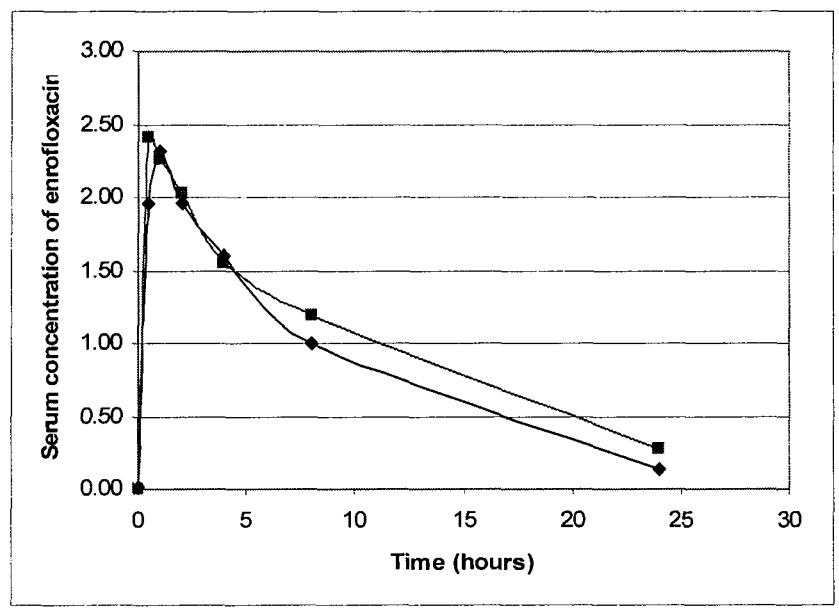
FIG. 7 is a graphical representation of the concentration of enrofloxacin in serum in µg/mL as a function of time (hours) when enrofloxacin is orally administered to three cats. The symbol (♦) represents data points for administration of a single tablet (22.7 mg) of commercially available enrofloxacin (i.e., Baytril) and the symbol (■), represents data points for administration of enrofloxacin as a liquid pharmaceutical formulation of the invention at a dose of 23 mg (i.e., 1 mL of a liquid composition of the invention having an enrofloxacin concentration of 23 mg/mL). Each data point is the average for three cats.

FIG. 7 is a graphical representation of the concentration of enrofloxacin in serum as a function of time. Each data point represents the serum concentration of enrofloxacin in µg/mL. Each data point represents the average of the serum concentration for the three cats. The symbol (♦) represents data points for administration of the solid dosage form of commercially available enrofloxacin (i.e., Baytril®) and the symbol (■) represents data points for administration of enrofloxacin as liquid pharmaceutical formulation of Example 13. The data demonstrates that the oral liquid formulation is bioavailable and that the bioavailability, as measured by area under the curve, is similar to, and in fact slightly better than, the bioavailability of Baytril®. The results demonstrate that the enrofloxacin when administered as the oral liquid pharmaceutical compositions of the invention have similar or improved bioavailability compared to Baytril® (i.e. fluoroquinolone in the acid form) even though salts of fluoroquinolones, particularly salts of fluoroquinolone with a divalent metal cation, are typically significantly less bioavailable compared to fluoroquinolone in the acid form. Without wishing to be bound by theory, it is believed that the improved bioavailability is due the formation of the complex $Mg^{+2}$(enrofloxacin)(GLY).

Example 15

Liquid Pharmaceutical Composition with Enrofloxacin, Magnesium Acetate, and Cyclodextrin 1.15 gr of enrofloxacin, 1.765 mL of de-ionized water, and 3.235 mL of 1M aqueous magnesium acetate solution (commercially available from Sigma-Aldrich of Milwaukee, Wis.) were combined in a 50 mL amber volumetric flask and the resulting composition mixed well using a vortex mixer. 20 mL of propylene glycol was then added to the volumetric flask and the resulting composition mixed well using a vortex mixer, with occasional sonication, to provide a clear solution. To the resulting clear solution was then added 3.6 g of β-cyclodextrin (commercially available from Sigma-Aldrich of Milwaukee, Wis.) and the solution mixed well using a vortex mixer. About 15 mL of glycerol was added to the volumetric flask and the resulting solution mixed well using a vortex mixer. The volumetric flask was then filled to a volume of 50 mL with glycerol and the solution mixed to provide the pharmaceutical composition. The concentration of enrofloxacin in the pharmaceutical composition is 23 mg/mL.

Example 16

Administration of Oral Liquid Enrofloxacin to Cats

A single tablet (22.7 mg) of commercially available enrofloxacin (Baytril®, commercially available from Bayer Health Care of Shawnee Mission, Kans.) was orally administered to each of three cats. 1 mL of the liquid enrofloxacin composition of Example 15 was orally administered to each of three cats. For each cat, the concentration of enrofloxacin in serum was determined as a function of time over a period of about 24 hours using the method described above in Example 4.

Figure 8:
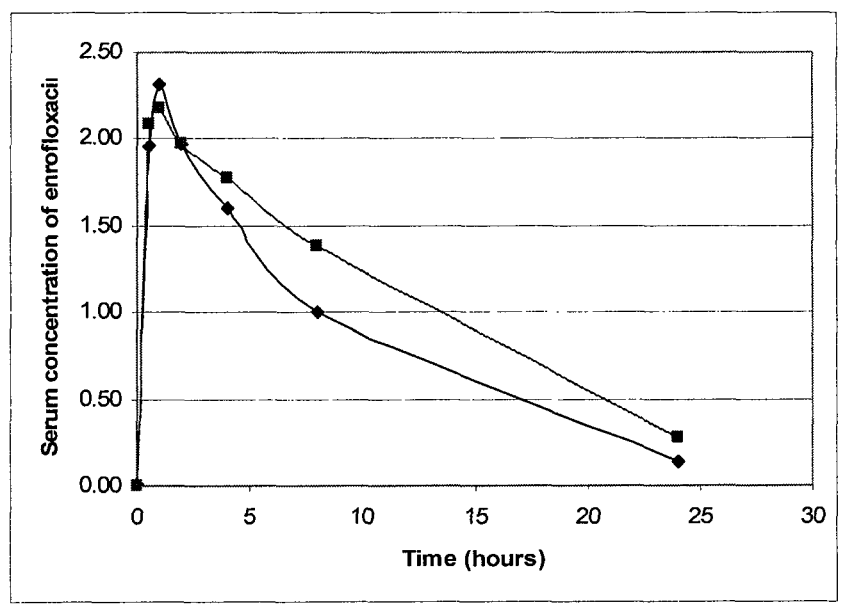
FIG. 8 is a graphical representation of the concentration of enrofloxacin in serum in µg/mL as a function of time (hours) when enrofloxacin is orally administered to three cats. The symbol (♦) represents data points for administration of a single tablet (22.7 mg) of commercially available enrofloxacin (i.e., Baytril) and the symbol (■), represents data points for administration of enrofloxacin as a liquid pharmaceutical formulation of the invention at a dose of 23 mg (i.e., 1 mL of a liquid composition of the invention having an enrofloxacin concentration of 23 mg/mL). Each data point is the average for three cats.

FIG. 8 is a graphical representation of the concentration of enrofloxacin in serum as a function of time. Each data point represents the serum concentration of enrofloxacin in µg/mL. Each data point represents the average of the serum concentration for the three cats. The symbol (♦) represents data points for administration of the solid dosage form of commercially available enrofloxacin (i.e., Baytril®) and the symbol (■) represents data points for administration of enrofloxacin as liquid pharmaceutical formulation of Example 15. The data demonstrates that the oral liquid formulation is bioavailable and that the bioavailability, as measured by area under the curve, is better than the bioavailability of Baytril®. The results demonstrate that the enrofloxacin in the oral liquid pharmaceutical compositions of the invention can have improved bioavailability compared to commercially available Baytril® (i.e. fluoroquinolone in the acid form) even though salts of fluoroquinolones, particularly salts of fluoroquinolone with a divalent metal cation, are typically significantly less bioavailable compared to fluoroquinolone in the acid form. Without wishing to be bound by theory, it is believed that the improved bioavailability is due the formation of the +2 complex $Mg^+$(enrofloxacin)(GLY) and/or $Mg^{+2}$(enrofloxacin)(PG). Without wishing to be bound by theory, it is also believed that the presence of the β-cyclodextrin in the pharmaceutical composition further stabilizes the $Mg^{+2}$(enrofloxacin)(GLY) and/or $Mg^{+2}$(enrofloxacin)(PG) complex, possibly by forming an inclusion complex, and/or by shifting the equilibrium to the complex.

Example 17

Stability of the Pharmaceutical Compositions

The pharmaceutical compositions of Examples 13 and 15 were stored at 70° C. (humidity not controlled) and analyzed daily by the following procedure:

A standard containing 100 mg of enrofloxacin is prepared by:
 1. Weigh 100 mg of enrofloxacin into a 100 mL volumetric flask;
 2. Add 5 mL methanol and about 50 mL 100 mM phosphate buffer pH 2.11 (prepared as described above for mobile phase A), mix well, and sonicate for about 1 minute to dissolve solids;
 3. Fill the flask to 100 mL with 100 mM phosphate buffer pH 2.11 to provide Dilution 1;
 4. Transfer 25 mL of Dilution 1 into a 50 mL volumetric flask, add 100 mM phosphate buffer pH 2.11 to a volume of 50 mL, and mix well to provide Dilution 2;
 5. Filter a portion of Dilution 2 into an HPLC vial using an Acrodisc 13 mm syringe filter with 0.2 µm membrane;
 6. Repeat steps 1-5 two more times to obtain three standards;
 7. Analyze each standard by HPLC using the following conditions:

| Column: | Waters X Bridge C-18 4.6 mm × 50 mm column equipped with a Gemini 4 mm × 3 mm guard cartridge. |
| --- | --- |
| Injection Volume: | 10 µL |
| Flow Rate: | 2 mL/min., isochratic 85% mobile phase A 15% mobile phase B |
| Mobile Phase: Composition: | |
| A: | 100 mM phosphate buffer - pH 2.1 |
| B: | Methanol |
| Acquisition Wavelength: | 274 nm |
| Run time: | 10 min. |

At the end of each analysis, the column is washed with 90 percent aqueous methanol.

8. Average the peak area obtained for each standard to provide an averaged peak area for the standard.

The pharmaceutical compositions of Example 13 and 15 were then analyzed by the following procedure to provide the amount of enrofloxacin at time 0 in each pharmaceutical composition:
 1. Weigh 40-120 mg of the pharmaceutical composition into a 20 mL scintillation vial;
 2. Add 5 mL of 100 mM phosphate buffer pH 2.11 (prepared as described above for mobile phase A) and shake well
 3. Filter a portion of this solution using an Acrodisc 13 mm syringe filter with 0.2 µm membrane into an HPLC vial to provide a time 0 sample;
 4. Repeat steps 1-3 twice to obtain a total of three time 0 samples;
 5. Analyze each time 0 sample by HPLC using the conditions described above;
 6. Average the peak areas for each of the time zero samples to provide an averaged peak area for the time 0 sample;
 7. Compare the averaged peak area for the time 0 sample to the averaged peak area for the standard averaged standards to obtain the actual amount of enrofloxacin in the pharmaceutical composition.

At various time points, t, a sample of the pharmaceutical composition of Example 13 or 15 stored at 70° C. was removed and analyzed following the procedure used to determine the amount of enrofloxacin as time 0 except that a single sample, rather than 3 samples, is analyzed. The peak area obtained by HPLC analysis for the time t sample is then compared to the averaged peak area for the time 0 sample to determine the percent of enrofloxacin in the time t sample relative to the time 0 sample.

The table provided below provides the percent enrofloxacin compared to time 0 as a function of time for the pharmaceutical compositions of Example 13 and Example 15 after storage at 70° C.

| | Percent enrofloxacin | |
| --- | --- | --- |
| Time (days) | Example 13 | Example 15 |
| 1 | 99.3 | 98.6 |
| 2 | 99.4 | 99.3 |
| 3 | 99.9 | 100.0 |
| 4 | 99.8 | 99.8 |
| 5 | 100.0 | 99.8 |
| 6 | 98.6 | 100.1 |
| 7 | 99.5 | 99.7 |
| 8 | 101.1 | 98.6 |
| 9 | 99.3 | 99.5 |
| 10 | 99.9 | 99.8 |

The results show that the pharmaceutical compositions of the invention have excellent stability even though they include a divalent metal cation. Typically, the pharmaceutical compositions of the invention show less than a 5 percent decrease in the amount of the fluoroquinolone after being stored at 70° C. for 10 days. In one embodiment, the pharmaceutical compositions of the invention show less than a 4 percent decrease in the amount of the fluoroquinolone after being stored at 70° C. for 10 days. In one embodiment, the pharmaceutical compositions of the invention show less than a 3 percent decrease in the amount of the fluoroquinolone after being stored at 70° C. for 10 days.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosure of which are incorporated herein by reference.

What is claimed is:
1. A pharmaceutical composition comprising:
   (i) a fluoroquinolone;
   (ii) a salt formed between a carboxylate anion and a divalent metal cation; and
   (iii) a liquid comprising an organic solvent selected from the group consisting of glycerol, glycerol formal, and mixtures thereof.
2. The pharmaceutical composition of claim 1, wherein the fluoroquinolone Is selected from the group consisting of ciprofloxacin, enrofloxacin, enoxacin, gatifloxacin, gemifloxacin, levofloxacin, lomefloxacin, moxifloxacin, norfloxacin, ofloxacin, sparfloxacin, trovafloxacin, difloxacin, cinofloxacin, pefloxacin, tosufloxacin, temafloxacin, fleroxacin, amifloxacin, binfloxacin, danofloxacin, marbofloxacin, ruflocaxin, and sarafloxacin.
3. The pharmaceutical composition of claim 1, wherein the divalent metal cation is selected from the group consisting of $Be^{+2}$, $Mg^{+2}$, $Ca^{+2}$, $Sr^{+2}$, $Ba^{+2}$, $Ra^{+2}$, $Cu^{+2}$, $Fe^{+2}$, and $Zn^{+2}$.
4. The pharmaceutical composition of claim 3, wherein the divalent metal cation is $Zn^{+2}$ or $Mg^{+2}$.
5. The pharmaceutical composition of claim 1, wherein the salt formed between an unsubstituted carboxylate anion and a divalent metal cation is zinc acetate.
6. The pharmaceutical composition of claim 1, wherein the salt formed between an unsubstituted carboxylate anion and a divalent metal cation is magnesium acetate.
7. The pharmaceutical composition of claim 1, wherein the liquid comprises glycerol.
8. The pharmaceutical composition of claim 1, wherein the liquid Comprises glycerol formal.
9. The pharmaceutical composition of claim 1, wherein the liquid further comprises water.
10. The pharmaceutical composition of claim 9, wherein the water is present in an amount of up to about 75 percent by volume of the liquid.
11. The pharmaceutical composition of claim 1, wherein the liquid comprises glycerol, glycerol formal, or a mixture thereof in an amount ranging from about 25 percent to 100 percent by volume of the liquid and water in an amount ranging from about 75 percent to 0 percent by volume of the liquid.
12. The pharmaceutical composition of claim 1, wherein the liquid comprises glycerol, glycerol formal, or a mixture thereof in an amount ranging from about 50 percent to 90 percent by volume of the liquid and water in an amount ranging from about 50 percent to 10 percent by volume of the liquid.
13. The pharmaceutical composition of claim 1, wherein the fluoroquinolone is present in an amount ranging from about 2 percent to 20 percent by weight of the pharmaceutical composition.
14. The pharmaceutical composition of claim 13, wherein the fluoroquinolone is present in an amount ranging from about 10 percent to 20 percent by weight of the pharmaceutical composition.
15. The pharmaceutical composition of claim 1, wherein the ratio of the fluoroquinolone to the salt formed between an unsubstituted carboxylate anion and a divalent metal cation ranges from about 3 to 0.5.
16. The pharmaceutical composition of claim 1, wherein the ratio of the fluoroquinolone to the salt formed between an unsubstituted carboxylate anion and a divalent metal cation ranges from about 2.5 to 0.8.
17. The pharmaceutical composition of claim 9, wherein the salt formed between an unsubstituted carboxylate anion and a divalent metal cation is zinc acetate, the liquid comprises glycerol in an amount of about 75 percent by volume of the liquid and water in an amount of about 25 percent water by volume of the liquid, and the ratio of fluoroquinolone to zinc acetate is about 2 to 1.
18. The pharmaceutical composition of claim 17, wherein the fluoroquinolone is selected from the group consisting of enrofloxacin, ciprofloxacin, and marbofloxacin.
19. The pharmaceutical composition of claim 9, wherein the salt formed between an unsubstituted carboxylate anion and a divalent metal cation is magnesium acetate, the liquid comprises glycerol in an amount of about 75 percent by volume of the liquid and water in an amount of about 25 percent water by volume of the liquid, and the ratio of fluoroquinolone to magnesium acetate is about 2 to 1.
20. The pharmaceutical composition of claim 19, wherein the fluoroquinolone is selected from the group consisting of enrofloxacin, ciprofloxacin, and marbofloxacin.
21. The pharmaceutical composition of claim 1, wherein the pharmaceutical composition is a solution.
22. The pharmaceutical composition of claim 1, wherein the composition is injectable.
23. The pharmaceutical composition of claim 9, wherein the pharmaceutical composition is a solution.
24. The pharmaceutical composition of claim 9, wherein the composition Is injectable.
25. The pharmaceutical composition of claim 1, wherein the pharmaceutical composition is prepared by adding the fluoroquinolone and the salt formed between an unsubstituted carboxylate anion and a divalent metal cation to glycerol, glycerol formal, or a mixture thereof.
26. The pharmaceutical composition of claim 9, wherein the pharmaceutical composition is prepared by adding the fluoroquinolone and the salt formed between an substituted carboxylate anion and a divalent metal cation to glycerol, glycerol formal, water, or any combination thereof.
27. A pharmaceutical composition comprising:
   (i) a fluoroquinolone;
   (ii) a salt formed between an unsubstituted carboxylate anion and a divalent metal cation;
   (iii) a liquid comprising an organ solvent selected from the consisting of glycerol, propylene glycol, glycol formal, and mixtures thereof; and
   a cyclodextrin.
28. A pharmaceutical composition comprising a complex of formula:

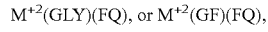

wherein:
FQ is a fluoroquinolone or an anion of a fluoroquinolone,
$M^{+2}$ is a divalent metal cation,
GLY is glycerol or an anion of glycerol, and
GF is glycerol formal or an anion of glycerol formal.

29. The pharmaceutical composition of claim 28, wherein the complex can be detected by mass spectral analysis.

30. The pharmaceutical composition of claim 28, further comprising a cyclodextrin.

31. A pharmaceutical composition comprising:
(i) a fluoroquinolone;
(ii) a salt formed between a carboxylate anion and a divalent metal cation;
(iii) a liquid comprising an organic solvent selected from the group consisting of glycerol, glycerol formal, and mixtures thereof; and
(iv) water;
wherein the pharmaceutical composition is obtained by combining the fluoroquinolone, the salt formed between a carboxylate anion and a divalent metal cation, and water to provide a first solution and then adding glycerol, glycerol formal, or mixtures thereof to the first solution within 24 hours of preparing the first solution.

32. The pharmaceutical composition of claim 31, further comprising a cyclodextrin.

33. A method of treating or preventing a condition in an animal comprising orally administering to the animal in need thereof, the pharmaceutical composition of claim 1.

34. The method of claim 33, wherein the bacterial infection as a bacterial infection caused by an organism selected from the group consisting of *Staphylococcus aureus, Streptococcus pneumoniae, coagulese-negative staphylococci, Streptococcus pyogenes, Staphylococcus epidermis, Pseudomonas aeruginosa, Escherichia coli, Klebsiella pneumoniae, Enterobacter cloacae, Proteus mirabilis, Proteus vulgaris, Providencia stuartii, Morganella morganii, Citrobacter diversus, Citrobacter freundii, Haemophilus influenzae*, or *Neisseria gonorrhea*.

35. The method of claim 33, wherein the bacterial infection is a respiratory tract infection, a urinary tract infection, a postoperative-wound infection, a bone or joint infection, a skin infection, an ear infection, or a sexually transmitted disease.

36. The method of claim 33, wherein the animal is selected from the group consisting of a canine, a feline, an equine, a bovine, an ovine, or a porcine.

37. The method of claim 36, wherein the animal is a cat.

38. The method of claim 36, wherein the animal is a dog.

39. The method of claim 33, wherein the composition is administered in an amount to provide a dose of the fluoroquinolone that ranges from about 0.1 mg/kg of body weight to 50 mg/kg of body weight.

40. The method of claim 39, wherein the pharmaceutical composition is administered daily or twice daily until 2-3 days after cessation of the bacterial infection.

41. The method of claim 39, wherein the pharmaceutical composition is administered for about 7 days.

42. The method of claim 39, wherein the pharmaceutical composition is administered for about 14 days.

43. The pharmaceutical composition of claim 1, wherein the pharmaceutical composition shows less than a 5 percent decrease in the amount of the fluoroquinolone after being stored at 70° for 10 days.

44. The pharmaceutical composition of claim 1, wherein the pharmaceutical composition show less than a 5 percent decrease in the amount of the fluoroquinolone after being stored at 70° C. for 10 days.

* * * * *

UNITED STATES PATENT AND TRADEMARK OFFICE
CERTIFICATE OF CORRECTION

Page 1 of 1

PATENT NO.        : 9,012,474 B2
APPLICATION NO.   : 12/210566
DATED             : April 21, 2015
INVENTOR(S)       : Yerramilli V. S. N. Murthy It is certified that error appears in the above-identified patent and that said Letters Patent is hereby corrected as shown below:

In the claims

Claim 1 at Column 31, line 26: replace "between a carboxylate anion" with --between an unsubstituted carboxylate anion--.

Claim 8 at Column 31, line 53: replace "Comprises" with --comprises--.

Claim 26 at Column 32, line 54: replace "substituted" with --unsubstituted--.

Claim 27 at Column 32, line 61: replace "organ" with --organic--.

Signed and Sealed this
Sixth Day of October, 2015

Michelle K. Lee
*Director of the United States Patent and Trademark Office*